(12) United States Patent
Campbell et al.

(10) Patent No.: US 7,742,877 B1
(45) Date of Patent: Jun. 22, 2010

(54) METHODS, APPARATUS AND COMPUTER PROGRAM PRODUCTS FOR FORMULATING CULTURE MEDIA

(75) Inventors: Robert L. Campbell, Bahama, NC (US); Perry D. Haaland, Chapel Hill, NC (US); Douglas B. Sherman, Durham, NC (US); Walter William Stewart, II, Cary, NC (US); Sheila A. Lloyd, Cary, NC (US)

(73) Assignee: Becton, Dickinson & Company, Franklin Lakes, NJ (US)

( * ) Notice: Subject to any disclaimer, the term of this patent is extended or adjusted under 35 U.S.C. 154(b) by 1295 days.

(21) Appl. No.: 09/359,260

(22) Filed: Jul. 22, 1999

(51) Int. Cl.
*G01N 33/48* (2006.01)
*G01N 31/00* (2006.01)
*G06G 7/48* (2006.01)
*G06G 7/58* (2006.01)

(52) U.S. Cl. .............................. 702/19; 702/22; 703/11; 703/12

(58) Field of Classification Search .................. 475/7.1
See application file for complete search history.

(56) References Cited

U.S. PATENT DOCUMENTS

| 5,510,240 A | 4/1996 | Lam et al. |
|---|---|---|
| 6,240,374 B1 * | 5/2001 | Cramer et al. ................. 703/11 |
| 2003/0162289 A1 | 8/2003 | Campbell et al. |

OTHER PUBLICATIONS

Tenson, Tanel et al., Journal of Biological Chemistry, 272:17425-17430, Jul. 1997.*
Ostrem, James A. et al., Biochemsitry, 37:1053-1059, Jan. 1998.*
"Webster's New World Dictionary, Third College Edition" (1988) Simon & Schuster, Inc.*
Hellberg et al., "Minimum Analog Peptide Sets for Quantitative Structure-Activity Relationships" *Int J Peptide Protein Res* (1991) 37:414-24.
Nomura, Kohji. Dec. 1986. "Specificity of prolyl endopeptidase." FEBS 4293, vol. 209, No. 2. pp. 235-237.
Odake, Shinjiro, et al. 1991. "Vertebrate Collagenase Inhibitor II. Tetrapeptidyl Hydroxamic Acids." Chem. Pharm. Bull., vol. 39, No. 6. pp. 1489-1494.
Patterson, C. A. And W. M. Ingledew. 1999. "Utilization of Peptides by a Lager Brewing Yeast." J. Am. Soc. Brew. Chem., vol. 57, No. 1. pp. 1-8.
Davis et al. 1973. "Corynebacterium Diphtheriae." pp. 682-692. (Omitted Book Title): Microbiology, Oct. 11, 2005.
Bause, Ernst. 1983. "Structural Requirements of N-glycosylation of Proteins." Biochemical Journal, vol. 209. pp. 331-336.
Vyas, Jatin M. et al. 1992. "Biochemical Specificty of H2M3." Journal of Immunology, vol. 149. pp. 3605-3611.
Invitrogen catalog, accessed from www.invitrogen.com on Jul. 27, 2005.
O'Shea et al. "Morphological Characterization of the Dimorphic Yeast Kluyveromyces marxianus var. marxianus NRRLy24I5 by Semi-Automated Image Analysis" Biotechnology and Bioengineering, (1996) vol. 51, pp. 679-690.
Automated Cell Technologies; In Vivo: The Business and Medicine Report, Windhover Information Inc., Dec. 1997, p. 38.
Cho et al.; *Rational Combinatorial Library Design. 2. Rational Design of Targeted Combinatorial Peptide Libraries Using Chemical Similarity Probe and the Inverse QSAR Approaches*, J. Chem. Inf. Comput. Sci., 38:259-268 (1998).
Cocchi et al.; *Amino Acids Characterization by GRID and Multivariate Data Analysis*, Quant. Struct.-Act. Relat. 12:1-8 (1993).
Gibbs et al.; *Some Factors Governing the Production of Diphtheria Toxin in Artificial Culture Media*, The Journal of Immunology, XIII:323-344 (1927).
Hellberg et al.; *Peptide Quantitative Structure-Activity Relationships, a Multivariate Approach*, J. Med. Chem. 30:1126-1135 (1987).
Kihara et al.; *Peptides and Bacterial Growth III. Utilization of Tyrosine and Tyrosine Peptides by Streptococcus faecalis*, The Journal of Biological Chemistry, 197:2 801-807 (1952).
Norinder; *Theoretical Amino Acid Descriptors. Application to Bradykinin Potentiating Peptides*, Peptides, 12:1223-1227 (1991).
Sneath; *Relations Between Chemical Structure and Biological Activity in Peptides*, J. Theoret. Biol., 12:157-195 (1966).
Zhao; *Isolation and Characterization of a Bacterial Growth-Stimulating Peptide from a Peptic Bovine Hemoglobin Hydrolysate*, Appl. Microbiol Biotechnol, 45:778-784 (1996).
Zheng et al.; *Rational Combinatorial Library Design. I. Focus-2D: A New Approach to the Design of Targeted Combinatorial Chemical Libraries*, J. Chem. Inf. Comput. Sci., 38:251-258 (1998).

* cited by examiner

*Primary Examiner*—Eric S DeJong
(74) *Attorney, Agent, or Firm*—Antonelli, Terry, Stout & Kraus, LLP.

(57) ABSTRACT

Methods, apparatus and computer program products are provided for identifying a component of culture medium based on the parameters (e.g., physical, chemical, biological and/or topological characteristics) of compounds from within a compound library. In preferred embodiments, the compound library is a peptide library. Also provided are methods of selecting a compound library from a larger compound space based on whole molecule (i.e., global) parameters of the compounds. Preferably, this method is practiced in conjunction with a method of identifying a component of a culture medium. Further provided are methods of predicting a biological activity of a peptide based on at least one whole molecule parameter of the peptide. This method finds use in methods of drug discovery, identifying components of culture medium, and identifying and/or designing peptides with particular pharmacological or therapeutic activities.

21 Claims, 8 Drawing Sheets

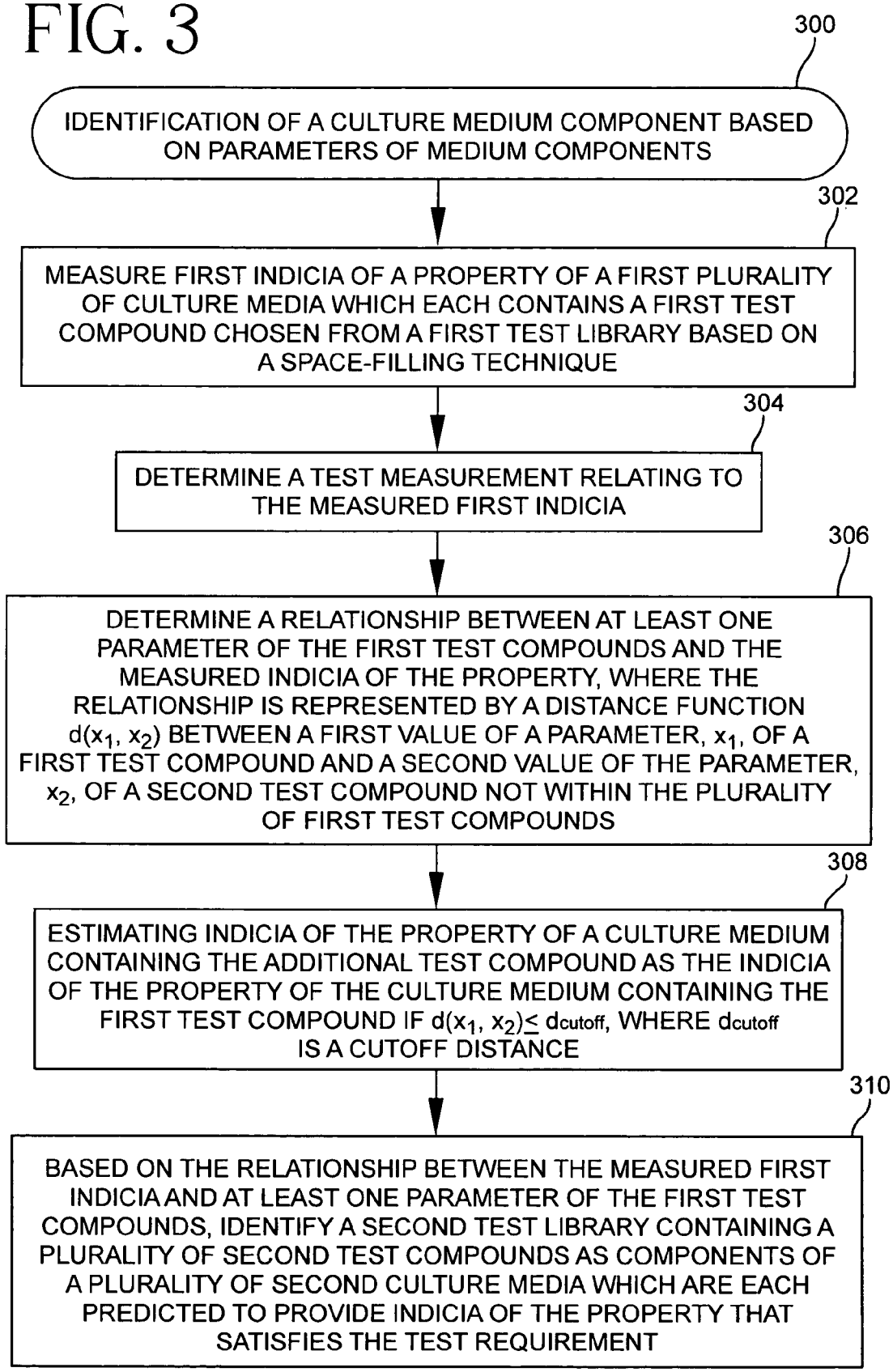

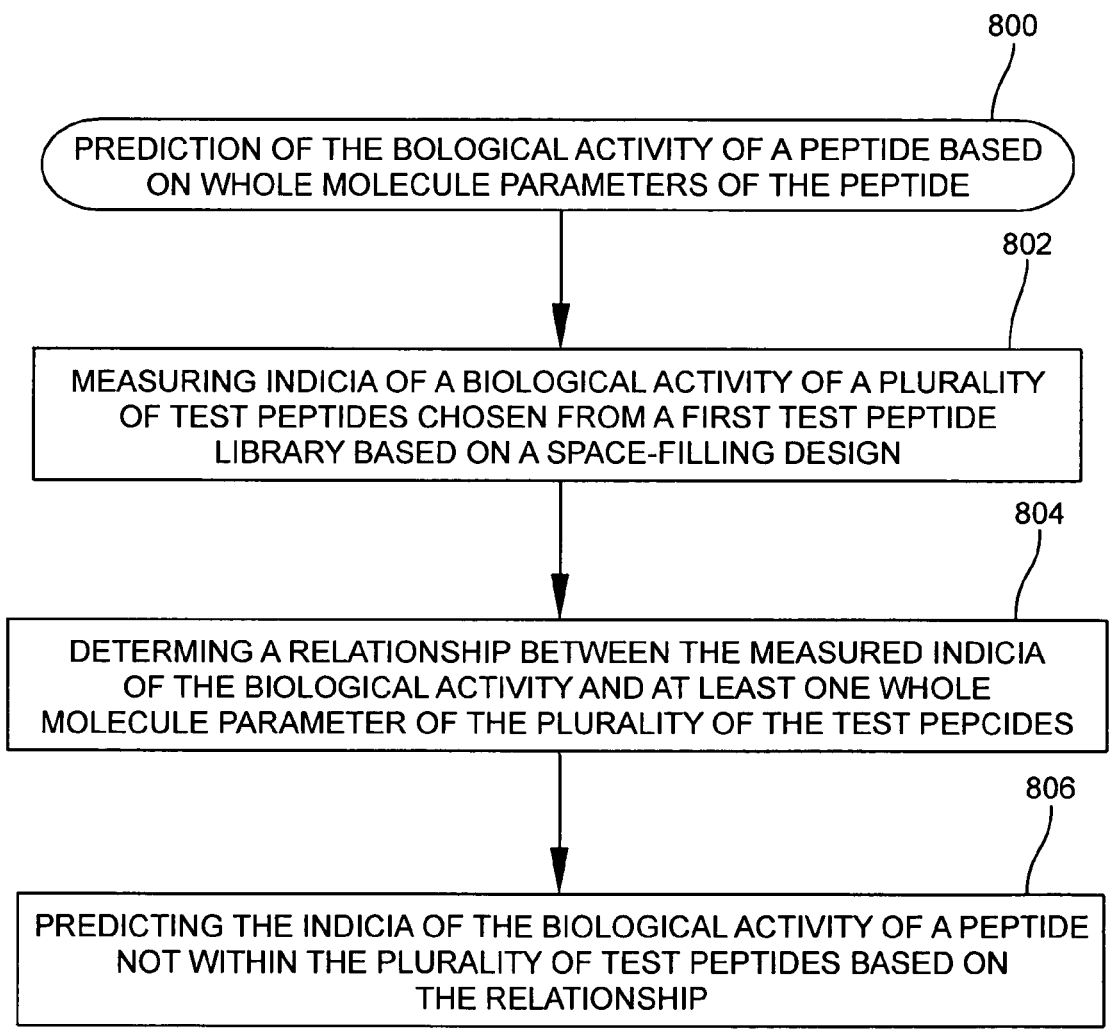

SEQUENCE LISTING

```
<160> NUMBER OF SEQ ID NOS: 49

<210> SEQ ID NO 1
<211> LENGTH: 4
<212> TYPE: PRT
<213> ORGANISM: Artificial Sequence
```

```
<220> FEATURE:
<223> OTHER INFORMATION: Description of Artificial Sequence:
      Hypothetical peptide

<400> SEQUENCE: 1

Gly Ala Leu Gly
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 2

Gln Gly Val Glu
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 3

Ser Ala Pro Val
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 4

Ser Pro Ala Gln
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 5

Glu Glu Val Phe
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 6

Val Leu Ser Lys
  1
```

```
<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 7

Val Ser Glu Leu
  1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 8

Pro Phe Glu Pro
  1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 9

Glu Leu Gln Glu
  1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 10

Lys Val Gln Phe
  1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 11

Gly Lys Ala Pro
  1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide
```

```
<400> SEQUENCE: 12

Ala Gln Lys Ser
 1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 13

Ala Gln Gly Glu
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 14

Lys Glu Phe Gly
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 15

Pro Ser Phe Lys
 1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 16

Phe Ser Leu Ala
 1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 17

Leu Phe Gly Ala
 1
```

```
<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 18

Glu Val Lys Ser
  1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 19

Val Gly Glu Ala
  1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 20

Gln Glu Ser Gln
  1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 21

Gly Ala Pro Val
  1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 22

Ser Ala Leu Gly
  1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide
```

```
<400> SEQUENCE: 23

Asp Lys Ala His
  1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 24

Asp Trp Pro Ala
  1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 25

Glu Ser Met His
  1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 26

Gly Val Asn Glu
  1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 27

His Glu Asp Val
  1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 28

Glu Thr Gly Ser
  1
```

```
<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 29

His Tyr Gly Val
  1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 30

Asp Phe Gly Val
  1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 31

His Tyr Pro Val
  1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 32

Ala Ala Ala Ala
  1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 33

Ala Ala Ala Cys
  1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide
```

```
<400> SEQUENCE: 34

Ala Ala Cys Ala
  1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 35

Ala Cys Ala Ala
  1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 36

Cys Ala Ala Ala
  1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 37

Ala Ala Cys Cys
  1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 38

Ala Cys Ala Cys
  1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 39

Cys Ala Ala Cys
  1
```

-continued

```
<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 40

Ala Cys Cys Ala
  1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 41

Cys Ala Cys Ala
  1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 42

Cys Cys Ala Ala
  1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 43

Ala Cys Cys Cys
  1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 44

Cys Ala Cys Cys
  1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide
```

```
<400> SEQUENCE: 45

Cys Cys Ala Cys
  1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 46

Cys Cys Cys Ala
  1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 47

Cys Cys Cys Cys
  1

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 48

Ser Val Val Val Val
  1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 49

Gly Ile Ile Leu Ser
  1               5
```

METHODS, APPARATUS AND COMPUTER PROGRAM PRODUCTS FOR FORMULATING CULTURE MEDIA

FIELD OF THE INVENTION

This invention relates to methods, apparatus and computer program products for formulating culture media, and more particularly to methods, apparatus and computer program products for identifying culture media components.

BACKGROUND OF THE INVENTION

Media used to grow cultured cells for both industrial and clinical applications are usually chemically undefined or, at best, semi-defined. It would be advantageous to employ chemically-defined media in cell culture systems; however, most attempts to grow cultured cells exclusively in chemically-defined media have been unsuccessful and result in a high frequency of cell death and/or poor cell performance. These efforts have failed, at least in part, because those components of undefined media that promote cell viability and performance remain uncharacterized. Thus, it would be desirable to develop improved methods of identifying media components that support and enhance cell viability and performance.

Hydrolysates are the most common undefined substance used in bacteriological media today for both clinical and fermentation applications. Current media optimization frequently starts with these undefined substances. Hydrolysates are used to replace serum (another undefined substance) in mammalian culture (Saha and Sen, (1989) *Acta Virol.* 33:338).

The inclusion of tissue and protein hydrolysates in bacterial growth media has been practiced since the late 1800s. Retger, (1927) *J. Immunology* 13:323, provided some of the earliest details on preparing and combining hydrolysates. Retger's data demonstrated that best toxin yields from *Corynebacteria diptheriae* were obtained with medium formulated with hydrolysates containing a lower percentage of full-length proteins and a higher concentration of peptides. Kihara et al., (1952) *J. Biol. Chem.* 197:801, also found that cultured cells performed better in medium containing peptides as compared with the constituent amino acids.

There are several drawbacks associated with using digests in cell culture media, for example, the range of peptide sequences available for incorporation into culture media is limited by the starting substrate and enzyme or acid used in the digestion. Many of the currently-available digests are difficult to reproduce, with significant lot-to-lot variation being commonplace. Digests of tissue obtained from a slaughterhouse are often used as components of cell culture media. These digests are among the most difficult to reproduce since the starting material and ratios of the starting substrate vary. Casein digests are more reproducible because milk is a more homogenous source of protein than slaughterhouse tissue. However, the range of peptide sequences generated by an enzymatic or acid digestion of casein is small. Most media manufacturers blend these two types of digest to yield a medium that provides better results than can be achieved with either digest used alone. Unfortunately, the use of blends adds another level of complexity to the manufacturing process and is also a source of lot-to-lot variability.

Moreover, both hydrolysates and sera are problematic for pharmaceutical applications, since each potentially harbors pathogens. The undefined nature of hydrolysates and sera also leads to problems in manufacturing. To illustrate, the high molecular weight components found in both types of undefined substances create additional downstream processing costs. Furthermore, the undefined nature of hydrolysates and sera leads to lot-to-lot variability. Previous attempts at developing chemically-defined media, however, have generally suffered from sub-optimal cell performance and unacceptable levels of cell mortality.

Historically, there have been several approaches employed to determine the type(s) of nutrients consumed or preferred by cells grown in culture. One of the most common practices is post-culture analysis, whereby the spent medium is evaluated to identify constituents removed from the medium. This approach has only rarely lead to the identification of compounds that can be isolated for use as a medium component or can be employed as a benchmark to monitor future hydrolysate or serum lots. In addition, this approach cannot identify compounds that function through signaling and are not physically removed from the medium.

Zhao et al., (1996) *Appl. Microbiol. Biotechnol.* 45:778, compared the bacterial growth-stimulating activity of bovine hemoglobin with that of specific peptides from a peptic hydrolysate of this protein. A particular peptide fragment was demonstrated to promote cell growth of gram negative bacteria to a greater extent than the intact protein. No such enhancement was observed when the constituent amino acids of this active fragment were assayed, leading these investigators to suggest that this peptide fragment did not simply act as an amino acid supplier, but rather interacted with peptide permeases on the cell membrane. This strategy can be employed in other systems as well to provide some information as to specific biologically-active peptides produced by hydrolysis of whole proteins.

More recently, Automated Cell Technologies (ACT; Pittsburgh, Pa.) has suggested that it will use a "combinatorial cell culture" to discover improved media for growing hematopoietic stem cells ex vivo. In Vivo: *Bus. Med. Rep.* 15:38 (December 1997). Utilizing a 384-well microtiter plate and a robotic pipetting system, ACT proposes to add different growth factor combinations to various mixes of culture media in an effort to identify a culture medium that will support stem cell growth ex vivo. It is unstated whether chemically-defined or undefined media will be used.

All of the previously-described methods fail to further an understanding of the physical, chemical or other properties of the medium components that contribute to the enhanced cell performance in culture. As a result, these methods are inefficient as they fail to provide a means of predicting and systematically screening additional lead compounds.

Most of the research on quantitative structure-activity relationships (QSAR) have focused on small organic molecules in medicinal and environmental chemistry. Peptides have not been studied as much owing to difficulties in developing descriptors for amino acid side chains. The earliest attempt to quantify amino acids for QSAR was by Sneath, (1966) *J. Theoretical Biology*, 12:157, who developed four semi-quantitative descriptors for amino acids. Later, Hellberg et al., (1987) *J. Med. Chem.* 30:1126, developed a set of principal components, which were derived from twenty-nine measured and theoretical properties of amino acids, including molecular weight, isoelectric point, nuclear magnetic resonance parameters, logP (hydrophobicity), thin layer chromatography, and high performance liquid chromatography parameters. Principle component analysis led to three principal components, which Hellberg et al. called $z1$, $z2$ and $z3$. Theoretically-derived parameters have been developed by Norinder, (1991) *Peptides,* 12:1223, and Cocchi and Johansson, (1993) *Quant. Struct.-Act. Relat.* 12:1. In all of these instances, parameters were developed for the individual amino acids, but none were measured on whole peptides.

Cho et al., (1998) *J. Chem. Inf. Comput. Sci.* 38:259, used a rational drug design approach to identify peptides in a targeted virtual library having bradykinin-potentiating activity. This group identified virtual peptides predicted to be enhanced in amino acid building blocks with bradykinin-like activity based on analysis of a starting set of peptides known to possess such activity. These investigators employed topological indices or physiochemical descriptors of individual amino acid building blocks from known leads to design a virtual targeted library. Cho et al. also report that computational limitations prevented complete analysis of all indices for every virtual peptide within their targeted library. Cho et al. did not apply their methods to media development.

Thus, previous attempts to improve culture media have largely relied on ad hoc trial-and-error techniques. There remains a need in the art for systematic and predictive methods for identifying medium components to improve cell performance in culture. Moreover, there is a need in the art for high through-put methods for identifying medium components.

SUMMARY OF THE INVENTION

Development of industrial and clinical culture media has been impeded, in large part, because of a lack of understanding as to which components of culture media promote cell performance. To compensate, currently-utilized media generally rely on the inclusion of complex and chemically-undefined substances, such as hydrolysates or serum, to support culture performance. The inability to identify and predict defined compounds for culture media formulations that will enhance culture performance is problematic, particularly in an industrial manufacturing setting where low cost, high performance, and reproducible systems are critical.

It is therefore an object of the present invention to provide methods, apparatus and computer program products for identifying culture medium components and for pairing new culture medium components with established media components.

It is also an object of the present invention to provide methods, apparatus and computer program products for predicting the activity (e.g., biological activity) of compounds from a compound library.

It is still another object of the present invention to provide methods, apparatus and computer program products for defining a test compound library from a larger compound space.

It is yet a further object of the present invention to provide methods, apparatus and computer program products for predicting an activity of a peptide based on parameters (i.e., descriptors) for whole molecules, constituent amino acids, or combinations thereof.

It is still a further object of the invention to provide more economical and rapid methods of identifying compounds with desired activities, e.g., for use in culture medium, drug discovery and therapy, and/or diagnostics.

These and other objects, features and advantages are provided by the present invention, which utilizes systematic design methods to identify lead compounds and to predict the structures of additional leads, e.g., for the formulation of culture media. Moreover, the present inventors have discovered that whole molecule descriptors of compounds (e.g., total dipole moment, molecular weight) can play an important (and in some cases, primary) role in predicting the activity of a compound and in more efficient exploration of compound space.

The media formulated by the present invention can result in improved products for diagnostic applications, for example, in products where the media is a single component such as plated media, or as a stand-alone product such as dehydrated culture media or liquid media. The new formulas may also enhance the manufacturing of products cultured in fermenters and bioreactors. In addition, the media formulated according to the present invention can provide an improved environment for cell research and drug discovery. In particular, the present invention can facilitate the development of culture media to maintain and propagate primary cells and cell lines that have been difficult to maintain in vitro in traditional media.

According to one preferred embodiment of the invention, a first test library of compounds is evaluated to identify compounds within the library with a desired characteristic(s) for use as a component of a culture medium. A plurality of culture media, each containing a respective test compound(s) from within the first test library, is screened by measuring an indicia of a property of the culture media. Typically, the indicia of the property is measured from a plurality of first cell cultures each containing a respective culture medium containing a respective test compound. Illustrative properties of the culture media containing the test compounds that may be measured according to the present invention include the ability to alter (e.g., induce or enhance, alternatively, suppress or inhibit) the growth of cultured cells, the ability to alter the production (e.g., at the level of transcription, translation, post-translational processing, intracellular transport, secretion, turnover, and the like) of a peptide(s) and/or protein(s) (e.g., antigens, toxins, antibodies, hormones, growth factors, cytokines, clotting factors, and enzymes), and the ability to alter the synthesis and/or secretion of other compounds including but not limited to antibiotics, steroids, carbohydrates, lipids and nucleic acids. Additional properties include the ability to alter (as defined above) the maturation, differentiation, growth and/or proliferation of cells.

In particular embodiments, a relationship (e.g., a mathematical relationship) is determined between at least one parameter or descriptor (e.g., physical, chemical, biological and/or topological parameters) of the test compounds from within the first test library which are included in the plurality of first culture media and the measured indicia of the property. The relationship can be used as a predictor to identify additional lead compounds as components of culture media that are expected, based on their parameters, to give indicia of the measured property that satisfy a test requirement. Illustrative parameters that may be employed according to the present invention include but are not limited to molecular weight, charge, isoelectric point, total dipole moment, isotropic surface area, electronic charge index, and hydrophobicity of the whole molecule (e.g., peptide, oligonucleotide, carbohydrate, lipid etc.) or individual building block (e.g., amino acid, nucleotide, monosaccharide, triglyceride etc.) in the molecule. Any suitable topological parameter known in the art may be employed, such as those described by L. B. Kier and L. H. Hall, Molecular Connectivity in Structure-activity Analysis, Research Studies Press, John Wiley & Sons, Letchworth England (1986); M. Johnson et al., Concepts and Applications of Molecular Similarity, John Wiley & Sons, New York (1990); and R. P. Sheridan et al., (1995) *J. Chem. Inf. Comput. Sci.* 35:310. The term "parameters" as used herein also encompasses the principle components of S. Hellberg et al., (1987) *J. Med. Chem.* 30:1126 (e.g., z1, z2, z3).

A test requirement is determined against which the measured indicia of the property are compared. The test requirement may be determined a priori or it may be determined before or after operations to determine a relationship between the parameter(s) of the first test compounds and the measured indicia of the property of the plurality of culture media containing the first test compounds. The test requirement may be determined so that indicia of the property falling above the test requirement are desirable. Alternatively, the test requirement may be chosen so that indicia of the property falling below the test requirement are preferred. As a further alternative, the test requirement may be such that indicia of the measured property that fall within a particular range are preferred (e.g., for cell growth, it may be advantageous to select for growth above a threshold level but below a maximum level, as growth rates above the maximum may adversely affect other aspects of cell performance). Alternatively, the test requirement may be qualitative, rather than quantitative, in nature.

The relationship is used to predict the structure of a plurality of untested compounds each of which, when included as a component of a culture medium, is expected to provide indicia of the property that satisfies the test requirement. Operations are also performed to identify a second test library containing a plurality of second test compounds as components of a plurality of second culture media. The plurality of second culture media, which each contain a respective test compound from within the second test library, are predicted to provide indicia of the property that satisfy the test requirement based on the relationship determined between the parameter(s) of the first test compounds and the first indicia of the measured property.

Optionally, and preferably, the plurality of second test compounds will include at least one compound that was not among the set of first test compounds. It is also preferred that the plurality of second test compounds includes one or more test compounds from within the first test library (i.e., as a control).

The steps of measuring indicia of a property of a plurality of culture media each containing a respective test compound, determining a relationship between the measured indicia and at least one parameter of the test compounds, and then determining a follow-up set of compounds may be carried out more than one time so as to identify a compound(s) that provides a desired indicia of the property when included as a component of culture media. Alternatively, if the first set of test compounds provides a compound having a desired activity, the screening process may end at that point without screening a second, or successive, set of test compounds.

The relationship determined between the parameter(s) of the first test compounds and the indicia of the measured property can be determined by any method for describing the interaction between the activity and structure of compounds, for example, by quantitative structure-activity relationships (QSAR), nearest neighbor analysis, self-organizing maps, or other machine learning and statistical techniques.

In one preferred embodiment, the relationship may be expressed in the form of $\hat{y}_i=(x_{ij})$, where $x_{ij}$ denotes a parameter, i ranges from 1 to n, where n represents the number of first culture media, j ranges from 1 to d, where d represents the number of parameters measured, and $\hat{y}_i$ represents an estimate of the measured first indicia of the property. The relationship represented by $\hat{y}_i=f(x_{ij})$ may be a parametric or nonparametric formula.

According to another preferred embodiment of the present invention, the relationship between the parameter(s) of the test compounds and the indicia of the measured property is based on a distance function between the parameters of the tested compounds in the first test library and the parameters of untested compounds. The distance function can be expressed as $d(x_1, x_2)$ between a first value of a parameter, $x_1$, of a first test compound and a second value of the same parameter, $x_2$, of a second untested compound. This relationship will assign to culture media containing a second untested compound an estimated indicia of the property that corresponds to the measured indicia determined from a culture medium containing a first tested compound from the first test library if $d(x_1, x_2) \leq d_{cutoff}$, where $d_{cutoff}$ is a cutoff distance for the first test compound. In other words, once a lead compound is identified from the first test library, additional lead compounds can be determined based on an assumption that compounds that are close in parameter space will exhibit similar activities. Accordingly, there is an increased probability that compounds close in parameter space will provide similar or better indicia of the measured property. In particular embodiments of the invention, $x_1$ and $x_2$ represent a single parameter or, alternatively, a set of parameters, i.e., $x_1=x_{11}, x_{12}, x_{13}, x_{14} \ldots x_{1k}$ and $x_2=x_{21}, x_{22}, x_{23}, x_{24} \ldots x_{2k}$, where $k \geq 1$. One specific example of a method of determining a relationship based on distance in parameter space is "nearest neighbor" analysis. Other non-limiting and illustrative methods are cluster analysis, self-organizing maps, and machine learning approaches. See generally, B. B. Ripley Pattern Recognition and Neural Networks, Cambridge University Press, New York (1996).

In still another particular embodiment, more than one relationship may be used to identify a plurality of second test compounds from within a second test library that are predicted to give indicia of the property that satisfy the test requirement when included as a culture medium component (e.g., both a QSAR-type and nearest neighbor-type relationship may be employed). Furthermore, the methods of the present invention described hereinabove are preferably practiced in an iterative fashion, whereby the lead compounds identified in the second test library can be used to determine additional lead compounds in a third test library, etc., until compounds that provide the desired characteristics are identified. Moreover, the relationship determined in each iteration need not be fixed. To illustrate, one type of relationship may be determined to identify a set of second test compounds, but a different relationship may be determined in subsequent iterations.

In addition, the inventive methods can be used to identify a "cocktail" of compounds for formulating culture media—the methods described hereinabove are not limited to media containing only a single test compound therein.

The second test library may be partially or completely co-extensive with the first test library (i.e., encompass some or all of the same compounds). Alternatively, there may be no common compounds in the first and second test libraries. The second test library will generally be smaller in size than the first test library, and may be a subset thereof.

The test compounds from the first and second test libraries may be selected using any suitable method known in the art. Preferably, the test compounds are selected from the compound space based on a space-filling design. It is further preferred that the test compounds selected from the compound space are representative of the entire compound space. Exemplary space-filling designs include but are not limited to full factorial designs, fractional factorial designs, maximum diversity libraries, genetic algorithms, coverage designs, spread designs, cluster based designs, Latin Hypercube Sampling, and other optimal designs (e.g., D-Optimal) and the like. The second test library can be selected from within the first test library or, alternatively, from within the compound space.

As a further alternative, the information obtained from screening a first compound space can be used to start screening a second compound space. For example, if the first compound space only contained tetrapeptides, the information and/or lead peptides achieved by screening the tetrapeptide space can be used to begin screening a pentapeptide space. As still a further alternative, and as described below, the first compound space may contain compounds of different sizes. According to this embodiment, in the preceding example it may not be necessary to go outside the first compound space if this space contained both tetrapeptides and pentapetides.

According to an additional preferred embodiment, the present invention provides a method of defining a test library from a larger compound space. Preferably, the test compound library will be representative of the compound space. In many instances, a compound space of interest may be so vast that it is computationally difficult to determine a test library therefrom. In particular, the space may be so large that it is not computationally feasible to evaluate the entire space in forming a test library. According to the present invention, the compound space can be reduced by grouping all compound isomers therein as single candidate compounds based on at least one global parameter or descriptor (e.g., compounds having the same molecular weight or chemical formula). Thus, each set or group of compound isomers can be represented as a respective candidate compound. The contraction of the compound space can advantageously simplify the process of determining the first test library (or a follow up library), and is based on the principle that compound isomers may exhibit similar activities because of shared whole molecule parameters (e.g., molecular weight, lipophilicity, charge—as compared with sequence-specific parameters). A test library can be selected from this reduced compound space, e.g., by using a space-filling design.

Optionally, and advantageously, after reducing the compound space, some of compound isomers within the reduced compound space are selected and expanded to re-introduce sequence-specific parameter(s) (e.g., z values, isotropic surface area, electronic charge index, hydrophobicity) of individual amino acids indexed to their relative positions in the sequence. In this expansion step, preferably less than all of the grouped candidate compounds in the reduced compound space are selected and are then re-expanded into their constituent compound isomers. A test library can be selected from the re-expanded set of constituent compound isomers. In one particular embodiment, the test library contains at least one representative compound from each expanded group of candidate compounds.

The test library is selected from the compound space using any suitable method known in the art. Preferably, the test library is selected based on a space-filling design as described hereinabove.

Another embodiment of the invention relates to test compound libraries generated by the above-described methods. The test compound library is selected from a larger compound space by representing each set of compound isomers in the compound space by a single compound. In preferred embodiments, the test library is formed from the reduced compound space by selecting less than all of the grouped candidate compounds and re-introducing sequence-specific parameters to re-generate the constituent compound isomers. In a more preferred embodiment, the test library is formed by selecting less than all of the constituent compound isomers. More preferably still, the test library is formed by selecting at least one compound from each of the re-expanded groups of constituent compound isomers.

According to another particular embodiment, the inventive methods of forming a test library by reducing (and optionally re-expanding) a compound space are employed in a method of forming a culture medium (as described hereinabove). These methods can be used to determine the first and/or the second test libraries as well as to determine subsequent follow-up libraries.

As still a further aspect, the present invention provides a method of predicting the activity of a peptide, preferably based on a whole molecule parameter(s) of the peptide. A relationship (e.g., a mathematical relationship) is determined between a measured indicia of an activity (e.g., a biological activity) of a plurality of peptides from a test peptide library and at least one parameter (preferably at least one whole molecule parameter) of the test peptides. Based on the relationship, the indicia of the activity of untested peptides can be predicted based on the parameter(s), preferably at least one whole molecule parameter, of the untested peptides. This method finds use, e.g., in rational drug design, in developing culture media, in methods of identifying and/or designing peptides that act as receptor agonists or antagonists, and in methods of identifying peptides that induce or enhance, or conversely prevent or inhibit, any activity of any target protein (e.g., a receptor or enzyme), cell, or nucleic acid (e.g., DNA and/or RNA).

In one particular embodiment, the method is used to identify a peptide with a predicted indicia of an activity that satisfies a test requirement. According to this embodiment, indicia of an activity of a plurality of test peptides from a first test peptide library are measured. A relationship is then determined between at least one parameter, preferably at least one whole molecule parameter, and the measured indicia of the activity of the test peptides. Those skilled in the art will appreciate that the relationship may also include sequence-specific parameters in addition to a whole molecule parameter(s). The relationship can be employed to determine a second test library containing a plurality of test peptides that are predicted to provide indicia of the activity that satisfies the test requirement.

In particular embodiments, the test peptide library is selected from a larger peptide space. In preferred embodiments, the peptide space is collapsed based on whole molecule parameters, and optionally re-expanded by re-introduction of sequence-specific parameters, prior to selecting the test peptide library therefrom, as described above.

Still another preferred embodiment of the present invention is an apparatus for identifying a compound(s) for forming a culture medium. The preferred apparatus comprises means for determining a relationship between the measured indicia of a property of a plurality of first culture media, each of which contain a respective first test compound from within a first test library and at least one parameter of the first test compounds. The preferred means further comprises means for identifying a second test library containing a plurality of second test compounds as components of a plurality of culture media, which based on the relationship, are expected to provide second indicia of the property that satisfy a test requirement. A computer program product is also provided for controlling the operation of the determining and identifying means and for performing numerical calculations to carry out the above-described operations.

In particular, a preferred computer program product comprises a computer-readable storage medium having computer-readable program code means embodied in the medium. The preferred computer-readable program code means comprises means for determining a relationship between measured indicia of a property of a plurality of first culture media each containing a respective test compound from within a first test library and at least one physical parameter of the first test compounds. Computer-readable program means is also provided for identifying a second test library containing a plurality of second test compounds as components of a plurality of second culture media, which based on the relationship between the measured first indicia and the parameter(s) are expected to provide indicia of the property which meets a test requirement relating to the measured first indicia. In addition, computer-readable program code means is also provided for performing more detailed ones of the above-described operations numerically. This embodiment of the present invention therefore provides a tool that can more accurately perform library screening to identify compounds for forming an improved culture medium.

Yet another preferred embodiment of the present invention is an apparatus for defining a test compound library. This preferred apparatus comprises means for representing each of a plurality of groups of compound isomers within a compound space as a candidate compound, so that the compound space is reduced, e.g., to facilitate computational manipulation and sampling thereof. Preferably, the apparatus further comprises means for defining a first test library by selecting and expanding less than all of the candidate compounds into their constituent compound isomers. It is further preferred that the apparatus comprises means for selecting a test library from the expanded compound isomers. A computer program product is also provided for controlling operation of the representing and defining means and performing numerical calculations to carry out the above-described operations.

A preferred computer program product comprises a computer-readable storage medium having computer-readable program code means embodied in the medium. The preferred computer-readable program code means comprises means for representing each of a plurality of compound isomers from within a first compound space as a respective candidate compound. Computer-readable program means is also provided for defining a first test library by expanding less than all of the candidate compounds into their constituent compound isomers. In addition, computer-readable program code means is also provided for performing more detailed ones of the above-described operations numerically. This embodiment of the present invention is therefore advantageous in that it provides a tool for defining a test compound library from a larger compound space.

These computer program products may be realized in whole or in part as software modules running on a computer system. Alternatively, a dedicated stand-alone system with application specific integrated circuits for performing the above-described operations may be provided.

These and other aspects of the invention are set forth in more detail in the description of the invention hereinbelow.

BRIEF DESCRIPTION OF THE DRAWINGS

FIG. 3 is a flow chart illustrating operations performed by methods, apparatus and computer program products according to a second embodiment of the present invention.

FIG. 8 is a flow chart illustrating operations performed by methods, apparatus and computer program products according to a fifth embodiment of the present invention.

DESCRIPTION OF THE PREFERRED EMBODIMENTS

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
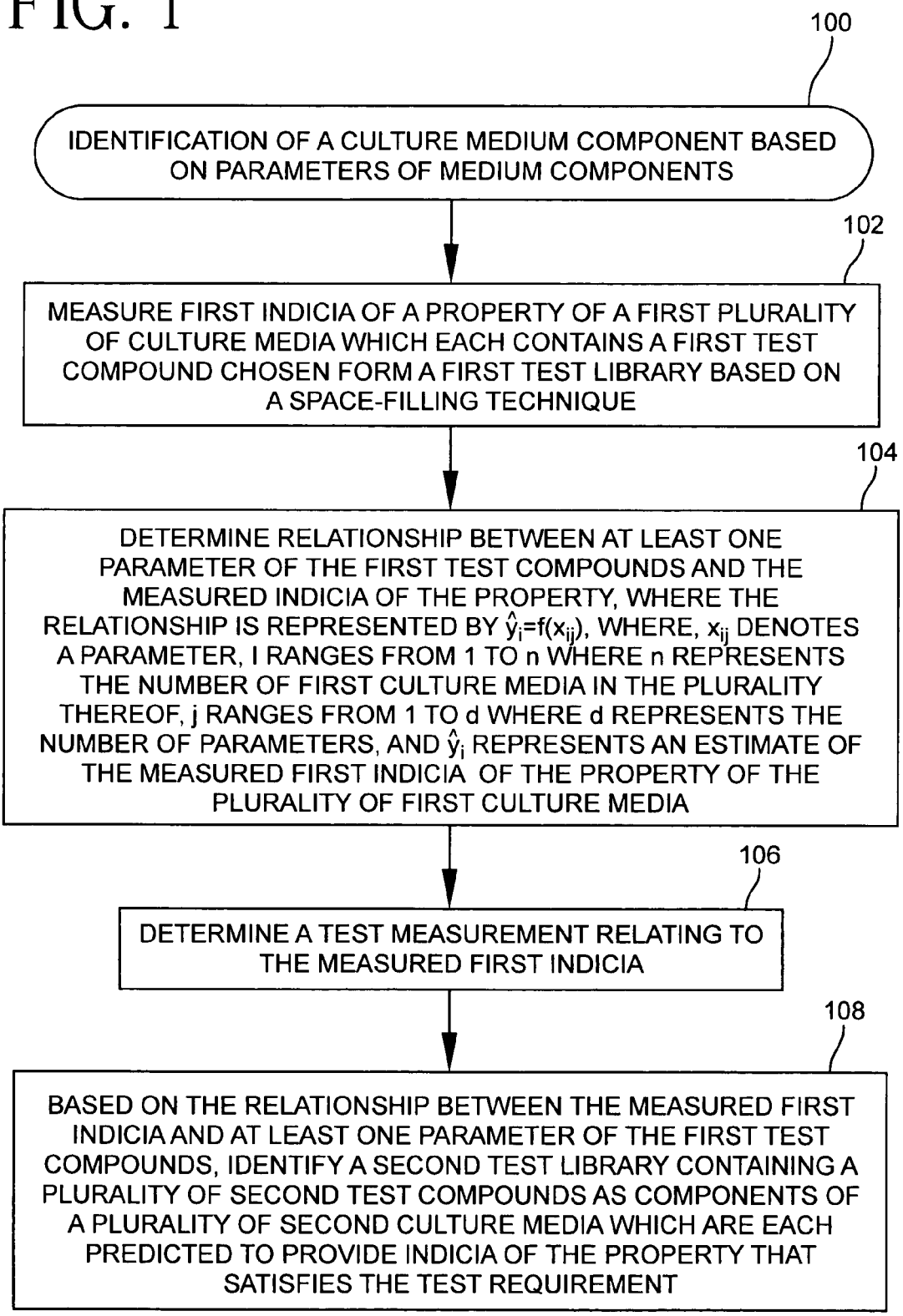
FIG. 1 is a flow chart illustrating operations performed by methods, apparatus and computer program products according to a first embodiment of the present invention.

Referring now to FIG. 1, preferred operations 100 for identifying a component of a culture medium use the parameter(s) or descriptor(s) (e.g., physical, chemical, biological and/or topological parameters) of compounds within a compound space to identify those compounds that are predicted to have a particular property (e.g., biological activity) when included as a component of a culture medium. The prediction is based on a relationship that is determined between measured indicia (e.g., quantitative level) of the property observed with known compounds. Alternatively, the measured indicia can be a qualitative measure (e.g., response/no response). The relationship is used to determine those untested compounds that are predicted to give desired indicia of the property based on the parameter(s) of the compounds.

The present invention can be employed to identify any type of polymeric compound of interest, preferably for use as a component of a culture medium. Exemplary classes of compounds include, but are not limited to peptides, proteins (including modified proteins, e.g., glycoproteins), lipids, carbohydrates, nucleic acids, and the like. Peptides are the preferred compound.

Compound libraries can be made by any method known in the art. Individual compounds within the libraries can be isolated and/or synthesized by any method known in the art. In particular, peptides can be synthesized by solid phase solution phase synthetic methods. For example, the peptides can be synthesized by FMOC chemistry (Atherton et al., (1989) *Solid Phase Synthesis: A Practical Approach*. IRL Press at Oxford University Press, Oxford, England) on an Advanced ChemTech Model 396 synthesizer. Alternatively, peptides may be synthesized using other variations of the Merrifield approach (Merrifield, (1965) *J. Am. Chem. Soc.* 85:2149), including Boc chemistry, synthesis on other solid supports (e.g., other resins, pins, etc., "tea-bag" synthesis (R. A. Houghten, (1985) *Proc. Nat. Acad. Sci. USA* 82:5131), and by combinatorial methods (e.g., split and divide). Peptides may also be synthesized to include modifications to the carboxyl terminus (e.g., esters, amides, etc.), the amino terminus (e.g., acetyl groups), and other non-naturally occurring amino acids (e.g., norleucine). Methods of oligonucleotide synthesis are also known in the art. See, e.g., Oligonucleotide Synthesis: A Practical Approach, M. J. Gait, ED, IRL Press: Washington, D.C., 1984. The generation of carbohydrate libraries is described, e.g., in Liang et al., (1996) *Science* 274:1520. Construction of RNA libraries are known in the art, e.g., by SELEX as described by C. Tuerck et al., (1990) *Science* 249:505.

This embodiment of the invention can be used to identify a compound(s) (as described above) for use as a component(s) of culture medium (e.g., cell culture medium, tissue culture medium, organ culture medium, and the like) having any property(ies) of interest. Exemplary properties include, but are not limited to, altering (e.g., enhancing or increasing, or in contrast, inhibiting or suppressing) the growth of cells in culture (e.g., cell division and/or cell size), altering production (e.g., at the level of transcription, translation, post-translational processing, intracellular transport, secretion, turnover, and the like) of a protein(s) and/or peptide(s) (e.g., antigens, toxins, antibodies, hormones, growth factors, cytokines, clotting factors, enzymes, and the like) by cells in culture, and altering the synthesis, processing and/or secretion of other compounds and/or metabolites (e.g., antibiotics, steroids, carbohydrates, lipids, nucleic acids, and the like). Additional properties include the ability to alter (as defined above) the maturation, differentiation, growth and/or proliferation of cells.

Those skilled in the art will appreciate that a compound may give different indicia of the property depending on the particular cell, tissue or organ to be cultured. Moreover, the indicia of the property may be affected by the base culture medium and/or the presence of other medium components. The culture medium can be used to culture any cell, tissue, or organ of interest. Preferably the culture medium is a cell culture medium. Typically, and preferably, the present invention is used to identify a component of culture medium to culture cells in vitro. In particular, the present invention can be practiced to culture animal (more preferably mammalian, avian or insect), plant, bacterial, protozoan, fungal, or yeast cultures. In addition, the culture medium can be one that is used to package viruses or bacteriophage in host cells. The present invention can also be advantageously employed to identify compounds for culture medium for cultures of primary cells (e.g., to grow β-islet cells for insulin production). Other uses of the present invention are to culture pathogenic organisms for diagnostic purposes, culture cells that have been genetically engineered to express recombinant peptides or proteins (e.g., biopharmaceuticals such as interferon, tissue plasminogen activator, antibodies; industrial enzymes, in particular, low yield industrial enzymes such as restriction enzymes, taq polymerases, synthetases, and the like), and to culture cells to isolate secondary metabolites for use as drugs (e.g., cephalosporins). Finally, the culture medium can be a liquid, semi-solid, or solid, culture medium. Preferably, the culture medium is a liquid medium.

Indicia of the property may be measured using any suitable method known in the art. For example, ELISAs or any other immunoassays relying on specific binding to an antibody or receptor may be employed. Typically, such methods will involve a radiolabeled, fluorescent or other detectable moiety (e.g., a dye or intercalator such as acridine orange for DNA). Measurements may also be determined using labels that produce signals detectable by spectrophotometry (including colorimetry and measurement of optical density), x-ray diffraction or absorption, magnetism, or enzymatic activity. Chemiluminescence and fluorescence lifetime measurements may also be utilized. Suitable labels include fluorophores, chromophores, radioactive isotopes, electron-dense reagents, enzymes, and ligands having specific binding partners (e.g., biotin-avidin). Alternatively, a flow-through assay such as those that employ surface plasmon resonance detection may be used.

Cell number and/or size can be readily assessed by methods known in the art, e.g., staining and visual observation, turbidity measurements, spectrophotometric methods (including colorimetry and measurement of optical density), counting with an automated cell counter and/or automated plate counter, measurement of total cellular DNA and/or protein, impedance of an electrical field, bioluminescence, carbon dioxide, oxygen or ATP production or consumption, and the like. Proteins and other compounds can be detected and/or quantified using standard analytical techniques such as chromatography, gel separation techniques, and the like. Likewise, methods of detecting nucleic acids are well-known in the art and include specific hybridization to probe sequences and amplification methods (e.g., polymerase chain reaction, strand displacement amplification, etc.). Carbohydrates can be detected by any method known in the art, including but not limited to, carbohydrate-specific staining (e.g., lectins or anthrone-based assays), spectrophotometric methods with dyes or copper, $A_{205}$ measurements, or gas-liquid chromatography.

Any measurement tool known in the art may be used to take measurements as described above, e.g., a spectrophotometer for absorption or colorimetric measurements, a fluorometer or flow cytometer for fluorescence measurements, a scintillation or gamma counter for radioactive measurements, and an automated cell counter, automated plate counter, or manual plate counter for cell number measurements. As a further example, a microwell reader can be used for fluorescence, absorbance or colorimetric measurements.

Referring again to FIG. 1, in carrying out this particular embodiment of the invention, a first plurality of culture media each containing a first test compound(s) is provided. Operations are performed to determine indicia of the property of interest for each of the culture media in the first plurality thereof, Block 102.

The first test compounds are selected from a first test library of compounds, preferably using a space-filling design. It is also preferable that the first test compounds be representative of the first test library. The term "space-filling design" as used herein is intended to be construed broadly and includes all such techniques known to those skilled in the art. Exemplary space-filling designs include but are not limited to full factorial designs, fractional factorial designs, maximum diversity libraries, genetic algorithms, coverage designs, spread designs, cluster based designs, Latin Hypercube Sampling, and other optimal designs (e.g., D-Optimal), and the like.

A space-filling design assists in selecting experimental design points. Ideally, all data would be gathered at every possible combination of the explanatory variables which may possibly affect the response of interest, in other words, fill the entire space. When the candidate space is very large and the number of possible values is large, it may not be feasible to enumerate all such possible combinations, much less physically gather the data. For example, it would generally not be feasible to evaluate all possible peptide tetramers or pentamers (i.e., 160,000 possible tetramers and 3,200,000 possible pentamers). Space-filling designs provide a strategy for gathering data at a set of design points, such that the data gathered will efficiently represent all candidate compounds, known as the candidate space. When no prior information or knowledge is available, one method of generating a space-filling design is to use a geometric distance-based criterion.

Two general categories of distance-based designs are minimax and maximin. Assume that C denotes a finite set of possible design points and that there is a distance function d on C×C such that (C, d) is a metric space. Consider subsets D of C of size n. D is called a distance-based design if the design criteria depends on the distance function d. The minimax criterion attempts to cover the experimental space by locating design points so as to minimize the maximum distance from any candidate point to the closest design point. More specifically, call D* a minimax distance design if $$\min_D \max_{y \in C} d(y, D) = \max_{y \in C} d(y, D*) = d* \text{ where}: d(y, D) = \min_{x \in D} d(y, x).$$

The maximin criterion tries to spread the design points in space so as to maximize the minimum distance between the pairs of design points. In particular, we call D° a maximin distance design if $$\max_D \min_{x, x' \in D} d(x, x') = \min_{x, x' \in D^\circ} d(x, x') = d^\circ$$

Maximin designs can be generated by Gosset (Hardin and Sloane, (1992) *Operating Manual for Gosset: A General Purpose Program for Constructing Experimental Designs* (2d ed.), Mathematical Science Research Center, AT&T Bell Laboratories, Murray Hill, N.J.).

Approximations to these criterion that are more numerically stable and can be found using an exchange algorithm, are the "coverage" and "spread" criteria, respectively. The maximin, or spread criterion, tends to produce designs with a large number of design points at the boundaries of the region or most extreme values, while the minimax, or coverage criterion, produces designs with more points in the interior of the region.

A coverage design minimizes the following criterion for a choice of parameters p and q:

$$c_{p,q}(C, D) = \left( \sum_{y \in C} (d_p(y, D))^q / N_C \right)^{1/q}$$

where the distance metric is defined as:

$$d_p(y, D) = \left( \sum_{x \in D} \|x - y\|^p / n \right)^{1/p}$$

where p<0 and q>0.

Alternatively, as another space-filling design, test libraries can be generated using a genetic algorithm. In general, a genetic algorithm is based on the model of natural selection. Genetic algorithms optimize structures by computationally performing selection, crossover, and mutation in a population of structures in a manner analogous to natural selection. A given population of compounds is encoded as binary structures ("chromosomes"), and their opportunity to "reproduce" and be included in succeeding generations is based on their biological activities. In the reproduction step, the chromosomes for two compounds are crossed at a single point to produce two new "children" compounds. Mutation occurs by randomly changing any single bit in the sequence. The chromosomes are then decoded into compound structures, which are then synthesized and tested, and the process is repeated for the next generation.

A typical genetic algorithm runs as follows:

Step 1. Initialize a population of chromosomes, i.e., compounds (this can be done completely at random by a computer, or selected structures can be used to "seed" the initial population).

Step 2. Evaluate each chromosome in the initial population (e.g., synthesize and test every peptide in the initial population).

Step 3. Create new chromosomes by mating current chromosomes; apply mutation and recombination as the parent chromosomes mate (this is done by feeding the indicia of the properties of the compounds into the computer, and the program performs the mutation and recombination process).

Step 4. Delete members of the population to make room for the new chromosomes (the population will always be fixed at a particular size. The program will select which compounds get deleted, which are usually the poorest-performing compounds).

Step 5. Evaluate the new chromosomes and insert them into the population.

Step 6. The process can end at this point, with the best chromosome(s) being selected; alternatively, additional generations can be followed by repeating steps 3-5.

To illustrate, the following example using model data is presented. In selecting a peptide library using a genetic algorithm, the chromosomes will be individual peptides. Each amino acid may be represented as a binary string. For a 4-bit string, there are 16 possible combinations (Table 1). If, for example, only 10 of the possible amino acids are used, 6 of these amino acids must be represented twice (e.g., Gly is represented by 1010 and 1011), so that all of the 16 possible combinations are assigned to an amino acid as follows:

TABLE 1

| Binary String | Amino Acid |
| --- | --- |
| 0000 | Val |
| 0001 | Glu |
| 0010 | Leu |
| 0011 | Pro |
| 0100 | Lys |
| 0101 | Ser |
| 0110 | Ala |
| 0111 | Val |
| 1000 | Phe |
| 1001 | Glu |
| 1010 | Gly |
| 1011 | Gly |
| 1100 | Ser |
| 1101 | Phe |
| 1110 | Gln |
| 1111 | Pro |

An initial population of tetrapeptides can be generated using a random number generator. Structures can be modified at this point because of possible synthetic difficulties or to ensure that each amino acid is represented at each position, etc. Assume the following set of chromosomes (peptides) are generated:

TABLE 2

| SEQ ID NO: | Peptides | Binary String |
|---|---|---|
| 1 | Gly-Ala-Leu-Gly | 1010011000101010 |
| 2 | Gln-Gly-Val-Glu | 1110101000000001 |
| 3 | Ser-Ala-Pro-Val | 0101011000110000 |
| 4 | Ser-Pro-Ala-Gln | 0101001101101110 |
| 5 | Glu-Glu-Val-Phe | 0001000100001000 |
| 6 | Val-Leu-Ser-Lys | 0000001001010100 |
| 7 | Val-Ser-Glu-Leu | 0000010100010010 |
| 8 | Pro-Phe-Glu-Pro | 0011100000010011 |
| 9 | Glu-Leu-Gln-Glu | 0001001011100001 |
| 10 | Lys-Val-Gln-Phe | 0100000011101000 |
| 11 | Gly-Lys-Ala-Pro | 1010010001100011 |
| 12 | Ala-Gln-Lys-Ser | 0110111001000101 |
| 13 | Ala-Gln-Gly-Glu | 0110111010100001 |
| 14 | Lys-Glu-Phe-Gly | 0100000110001010 |
| 15 | Pro-Ser-Phe-Lys | 0011010110000100 |
| 16 | Phe-Ser-Leu-Ala | 1000010100100110 |
| 17 | Leu-Phe-Gly-Ala | 0010100010100110 |
| 18 | Glu-Val-Lys-Ser | 0001000001000101 |
| 19 | Val-Gly-Glu-Ala | 0000101000010110 |
| 20 | Gln-Glu-Ser-Gln | 1110000101011110 |

If, for example, the computer decided to cross Gly-Ala-Leu-Gly (SEQ ID NO:1) and Ser-Ala-Pro-Val (SEQ ID NO:3) at their mid-points, it would generate two new children chromosomes/peptides to the population to test: Gly-Ala-Pro-Val (SEQ ID NO:21) and Ser-Ala-Leu-Gly (SEQ ID NO:22).

Genetic algorithms are described in more detail, e.g., in J. Sing et al., (1996) *J. Am. Chem. Soc.* 118:1669 and *Handbook of Genetic Algorithms*, Lawrence Davis, Ed., Van Nostrand Reinhold: New York, 1991.

Referring back to FIG. 1, the test compounds can be all or a subset of the compounds in the first test library. The first test library can be selected on the basis of any criterion known in the art. For example, the first test library may include all possible pentapeptides (naturally occurring and/or non-naturally occurring). Alternatively, the first library may contain all possible pentapeptides based on a set of ten possible amino acids. As a further non-limiting example, all of the compounds in the first test library may have a specific subunit designated in a particular position(s) (e.g., the first amino acid may always be an alanine or an aromatic amino acid). It is not necessary that all of the test compounds in the first test library actually be synthesized and/or isolated, e.g., the library may be a "virtual" library. Typically, it is only necessary that the test compounds for which an indicia of the property is determined actually be synthesized, alternatively isolated, and evaluated. Alternatively, it is possible that indicia of the property of a particular compound(s) may be determined from other sources (e.g., the literature or from previous studies or studies from other investigators) and, therefore, this compound(s) would not have to be synthesized and a measurement of the indicia of the property of interest determined.

It is preferred that the present invention be carried out to screen a peptide library to identify peptides for use as components of culture medium. There are no particular requirements of the peptide library to be used to carry out this embodiment of the invention. The peptides in the library may contain naturally-occurring and/or synthetic amino acids. The library may also contain modified amino acids (e.g., phosphorylated, methylated, glycosylated, and the like). Moreover, the peptide library can be defined to contain less than all of the possible naturally-occurring and/or synthetic amino acids. The peptide library may also be defined so that all of the peptides therein have the same length or range of lengths. Alternatively, the peptides in the library may vary in length, e.g., tetramers, pentamers and/or hexamers. Peptide libraries in which all of the peptides have the same length (e.g., 4, 5, 6, 7, 8, 9, 10 or more amino acids) are preferred. In preferred embodiments, the peptide library contains peptides having a length of four, five, six, seven, eight, nine, or ten amino acids, or longer. In other preferred embodiments, the peptide library contains peptides having a length in a range from about four amino acids to about twenty amino acids, more preferably, from about four amino acids to about ten amino acids.

In alternate preferred embodiments, one or more amino acid positions in the peptides is fixed (i.e., nonvariable) or limited to specified particular amino acid(s) or class(es) of amino acids. For example, in a library of pentapeptides, the amino acids at positions 4 and 5 might be fixed as a specific amino acid (e.g., Ala or Val) or class of amino acids (e.g., aromatics). Likewise, the peptides may be 20-mers, but only 5 of the positions may be variable with the other positions being fixed. The positions may be fixed based on any criteria, e.g., random assignment, prior chemical knowledge, ease of manufacturing and/or synthesis, cost, and the like.

Those skilled in the art will appreciate that fixing or limiting the possible amino acid(s) at a particular position or positions will reduce the total number of possible peptides and may likewise decrease the time, expense and/or technical difficulties associated with synthesizing and testing peptides, identifying leads, and follow up (if necessary).

As a further aspect, the present invention provides a method of screening a compound library (preferably a peptide library) in which at least one of the amino acid positions is nonvariable or limited to designated subunits (i.e., less than all possible subunits, e.g., amino acids). A compound of interest, e.g., as a component of a culture medium, may be identified in the first round of screening. Alternatively, leads are identified and successive screenings are performed as described herein.

Operations are performed to determine a desired indicia, or alternatively range of indicia, of the property to establish a test requirement against which the measured indicia of the property of the media containing the test compounds are compared, Block 106. The test requirement may be determined at any stage in the process of identifying a culture medium component. For example, the test requirement may be set a priori or, alternatively, it may be determined after the indicia of the property of the first plurality of culture media each containing a first test compound is determined. Moreover, the test requirement may change during the compound screening process.

The test requirement may represent a threshold level and indicia of the property falling at or above the test requirement may be desirable (e.g., when screening for compounds that increase antibiotic production) or it may represent a ceiling and values falling below the test requirement may be desirable (e.g., when screening for compounds that suppress endotoxin production during fermentation processes). As a further alternative, the test requirement may relate to a range of desired indicia, i.e., the test requirement may establish both a floor and a ceiling for the measured indicia (e.g., to reach a balance between competing factors, such as cell growth and protein production). Those skilled in the art will appreciate that the test requirement may represent the optimal indicia of the property (e.g., maximal immunogen production), alternatively, the test requirement may take into account other criteria such as feasibility, cost, time constraints, effects on other desired properties of the culture medium, etc.

As yet a further alternative, the test requirement may be qualitative, rather than quantitative, in nature, e.g., if one is looking for the absence/presence of a particular response (i.e., a yes/no answer). Those skilled in the art will recognize that for computational analysis of qualitative data, the qualitative values will most likely be converted into quantitative values (e.g., response/no response →1/0)

Operations are performed to determine a relationship between at least one parameter of the first test compounds and the measured indicia of the property for each of the first test compounds, Block 104. Preferably, the relationship is a mathematical relationship, more preferably a mathematical structure-activity relationship between the parameter(s) and the property (i.e., activity) of interest. There is no particular limit to the number of parameters used to determine the relationship, and two, three, four, five, six, seven, eight, nine, ten or more parameters can be used. In one illustrative example, a relationship is determined between three parameters (molecular weight, hydrophobicity, total charge) of a plurality of peptides and the measured cell growth or β-toxin production by cultures of *Clostridium perfringens*.

Any parameter (i.e., descriptor) known in the art that can be applied to characterize a compound may be used to carry out the present invention. Physical, chemical (including biochemical), biological and/or topological parameters may be employed to determine the relationship. The term "parameter" as used herein is also intended to encompass the principle components of S. Hellberg et al., (1987) *J. Med. Chem.* 30:1126 (e.g., z1, z2, z3). The parameter(s) used to describe the test compounds can change in both number and type during the selection process. In addition, the parameter(s) can be a whole molecule parameter(s), sequence specific parameter(s), or a combination of both.

Preferably, the compounds are characterized using at least one whole molecule parameter (e.g., one, two, three, four, five, six, seven, eight, nine, ten or more whole molecule parameters). Also preferred are embodiments wherein the compounds are characterized using only whole molecule parameters. A "whole molecule parameter" is a value that characterizes a molecule irrespective of the arrangement of its constitutive atoms. For example, a whole molecule parameter for a peptide is one that does not depend on the order or sequence of the amino acids in the peptide. Describing a molecule using at least one whole molecule parameter may facilitate the compound screening process because it reduces (i.e., collapses) the size of the compound space and can thereby decrease the time, computational difficulty, and cost of screening large compound spaces (as described in more detail below).

Conversely, a "sequence-specific" parameter is one that is dependent on the specific order or sequence of the constitutive atoms or subunits. Examples of particular sequence-specific and whole molecule parameters have been provided hereinabove.

Illustrative parameters that may be employed according to the present invention include but are not limited to molecular weight, charge, isoelectric point, total dipole moment, isotropic surface area, electronic charge index, and hydrophobicity (e.g., as exemplified by measurements such as logP, HPLC retention times, or other methods of determining hydrophobicity known in the art) of the whole molecule or individual building block in the molecule (e.g., peptide, amino acid, nucleic acid, sugar unit, etc.). Any suitable topological parameter known in the art may be employed, such as those described by L. B. Kier and L. H. Hall, Molecular Connectivity in Structure-activity Analysis, Research Studies Press, John Wiley & Sons, Letchworth England (1986); M. Johnson et al., Concepts and Applications of Molecular Similarity, John Wiley & Sons, New York (1990); and R. P. Sheridan et al., (1995) *J. Chem. Inf. Comput. Sci.* 35:310.

Calculations of parameters can be carried out by any method known in the art, for example, using a computerized system, e.g., a Silicon Graphics computer or a PC. Total charge, molecular weight, and total dipole can be calculated using Sybyl 6.5 (Tripos). Moriguchi logP (i.e., mlogP, a measure of hydrophobicity) can be calculated using a Sybyl Programming Language Script. Literature values of electronic charge index and isotropic surface area for amino acids are available, see, e.g., E. R. Collantes et al., (1995) *J. Med. Chem.* 38:2705. A variation of electronic charge index can be prepared in an analogous manner using Gasteiger charges supplied by Sybyl instead of CNDO/2 charges used by Collantes et al. (Id). Principal component descriptors z1, z2, and z3 are provided by Hellberg et al., (1987) *J. Med. Chem.* 30:1126. Calculations of the isoelectric point can be carried out using a Sybyl Programming Language Script.

The relationship between the at least one parameter of the test compounds and the measured indicia of the property for each of the test compounds is used to identify a second plurality of culture media. Each of the second culture media contains a second compound(s) from within a second test library, where the second plurality of culture media are predicted to give indicia of the property that satisfy the test requirement, Block 108. Typically, the second test compounds will be untested compounds although those skilled in the art will appreciate that one or more compounds from the first set of test compounds may be included in the second set of test compounds, e.g., as controls.

In particular embodiments, the second test library includes all compounds that are predicted to satisfy the test requirement. Alternatively, and preferably, the second test library is chosen to include a subset of the total number of compounds that satisfy the test requirement. The second set of test compounds may include all of the test compounds in the second test library or, alternatively, a subset thereof. For example, the second test library may include all peptides having five amino acids that are predicted to result in antibody production from cultured hybridoma cells above a particular level (i.e., the test requirement) when added to culture medium. Alternatively, and preferably, the second test compounds are selected from, and more preferably are representative of, the second test library. Yet more preferably, the second test compounds are selected from the second test library using a space-filling design, as described above.

In particular embodiments of the invention, indicia of the property of the second plurality of culture media are measured, and the indicia compared with the test requirement. A lead compound may be identified at this stage that satisfies the test requirement. Alternatively, the above-described process of FIG. 1 is carried out in an iterative fashion. A second relationship between at least one parameter of the second test compounds and the measured indicia will be determined, and a third set of test compounds from a third compound library is identified. As a further alternative, if the first test library provides a suitable compound, the screening process can end there without the need to generate a second test library or to engage in further compound screening.

Those skilled in the art will appreciate that the systematic methods described hereinabove can be supplemented by knowledge of the chemical behavior to select a follow-up library of compounds. For example, in screening a peptide library, it may become apparent that peptides containing amino acids with large aromatic groups exhibit desired indicia of the property. Accordingly, a follow-up library may be chosen that is enriched in such peptides. Alternatively, if a desired end product was composed of an abundance of one or more types of amino acids, peptides containing these amino acids might be selected for screening, in particular if it is known that the particular cell line cannot synthesize any or sufficient quantities of the amino acid(s). As a further alternative, one may choose to make the carboxyl-terminal groups of a peptide as amides or acids based on prior knowledge, e.g., these features are known to enhance activity. Similarly, one might synthesize one library of peptides that all have carboxyl-terminal acids and a second library of peptides with carboxyl-terminal amides. If one library performs better than the other, one might only use peptides with carboxyl-terminal acids or amides for the remainder of the screening iterations.

In one preferred embodiment of the invention, as diagrammed in FIG. 1, the relationship may be expressed in the form of $\hat{y}_i = f(x_{ij})$, where $x_{ij}$ denotes a parameter, i ranges from 1 to n, where n represents the number of first culture media, j ranges from 1 to d, where d represents the number of parameters measured, and $\hat{y}_i$ represents an estimate of the measured first indicia of the property, Block 104. The relationship represented by $\hat{y}_i = (x_{ij})$ may be a parametric or non-parametric formula.

In one particular embodiment, the relationship is a quantitative structure-activity relationship (QSAR). This aspect of the invention can be demonstrated using an illustrative example, as follows.

The present invention may be used to identify a peptide to include as a component of a culture medium. The culture medium may be used to culture bacterial cells genetically engineered to produce a heterologous protein of interest. Accordingly, it would be desirable to identify a peptide which when included in a culture medium will enhance protein production by bacterial cells grown in the culture medium (i.e., to satisfy a test requirement).

In this example, eight test peptides are selected from a tetrapeptide library: Asp-Lys-Ala-His (SEQ. ID. NO:23), Asp-Trp-Pro-Ala (SEQ. ID. NO:24), Glu-Ser-Met-His (SEQ. ID. NO:25), Gly-Val-Asn-Glu (SEQ. ID. NO:26), His-Glu-Asp-Val (SEQ. ID. NO:27), Glu-Thr-Gly-Ser (SEQ. ID. NO:28), His-Tyr-Gly-Val (SEQ. ID. NO:29, and Asp-Phe-Gly-Val (SEQ. ID. NO:30); Table 3. The test peptides may be selected from the library by any means known in the art. The values for three parameters (molecular weight, total charge, and mlogp, i.e., hydrophobicity) may be determined for each of the eight peptides. The indicia of the property, in this example a particular biological activity (i.e., protein production), may be determined for the eight peptides as well. The exemplary data are shown in Table 3.

TABLE 3

| SEQ ID NO: | Peptide | Hydrophobicity | Mol. Wt | Total Charge | Biol. Act. |
|---|---|---|---|---|---|
| 23 | Asp-Lys-Ala-His | −3.479 | 469.499 | 0 | 15.0 |
| 24 | Asp-Trp-Pro-Ala | −1.608 | 486.505 | −1 | 25.0 |
| 25 | Glu-Ser-Met-His | −3.479 | 501.535 | −1 | 19.3 |
| 26 | Gly-Val-Asn-Glu | −3.421 | 416.411 | −1 | 14.4 |
| 27 | His-Glu-Asp-Val | −4.03 | 496.477 | −2 | 18.5 |
| 28 | Glu-Thr-Gly-Ser | −4.25 | 391.357 | −1 | 10.2 |

TABLE 3-continued

| SEQ ID NO: | Peptide | Hydrophobicity | Mol. Wt | Total Charge | Biol. Act. |
|---|---|---|---|---|---|
| 29 | His-Tyr-Gly-Val | −1.278 | 474.518 | 0 | 23.6 |
| 30 | Asp-Phe-Gly-Val | −1.616 | 435.457 | −1 | 22.0 |

Using regression analysis, e.g., with the program S-Plus (Version 3.4 for Solaris, Mathsoft, Seattle, Wash.), the following equation can be derived to describe the relationship between the three parameters and the (hypothetical) indicia of the property (i.e., biological activities) of the first set of test compounds.

$$\hat{y} = 3.64 * \log P + 0.056 * MW - 1.97 * \text{charge} + 1.73 R^2 = 0.999 \quad (1)$$

where $\hat{y}$ is an estimated indicia of the property, logP is a measure of hydrophobicity, and MW is molecular weight.

If a satisfactory peptide (i.e., satisfies the test requirement) is not is identified among the first set of test peptides, the screening process will continue. A second set of untested peptides can then be selected by any means known in the art, and the parameter for the second set of peptides may be calculated. Using Equation 1, the predicted activity of a second set of culture media, where each of the culture media in the set contains one of the second test peptides, can be calculated for each culture media in the second set based on the parameters of the peptide included therein. For example, a predicted activity of 28.2 was derived for a culture medium containing the untested peptide His-Tyr-Pro-Val (SEQ ID NO: 31; Table 4). This value is higher than any of the biological activities in the original library, and, thus, this peptide would be a good candidate for synthesis and testing.

TABLE 4

| Predicted Peptide | Hydrophobicity | Mol. Wt | Total Charge | Predicted Biol. Act. |
|---|---|---|---|---|
| His-Tyr-Pro-Val (SEQ ID NO:31) | −0.645 | 514.583 | 0 | 28.2 |

If the test requirement is for protein production at a level of at least 25, then the compound screening process may end with the identification of His-Tyr-Pro-Val (SEQ ID NO:31) (assuming the actual biological activity is equal to the predicted activity). Alternatively, if the test requirement is set for protein production of at least 30, then the screening process would continue. The actual indicia of the property of a second set of culture media, each containing one of the second test peptides, may be determined. From these measurements, a new relationship between at least one parameter and biological activity is calculated. From this updated equation, a third set of peptides, which when included in culture media are predicted to promote protein production by the bacteria at a level of 30 or greater are identified. Typically, this process can continue in an iterative fashion until a peptide having the desired biological activity is identified.

Likewise, if the test requirement was set at a level of at least 20, then three of the original test peptides would satisfy the test requirement (e.g., Asp-Trp-Pro-Ala (SEQ. ID. NO:24), His-Tyr-Gly-Val (SEQ. ID. NO:29), and Asp-Phe-Gly-Val (SEQ. ID. NO. 30); Table 3), and the compound screening process could stop at this point or could continue to look for even better performing peptides.

Figure 2:
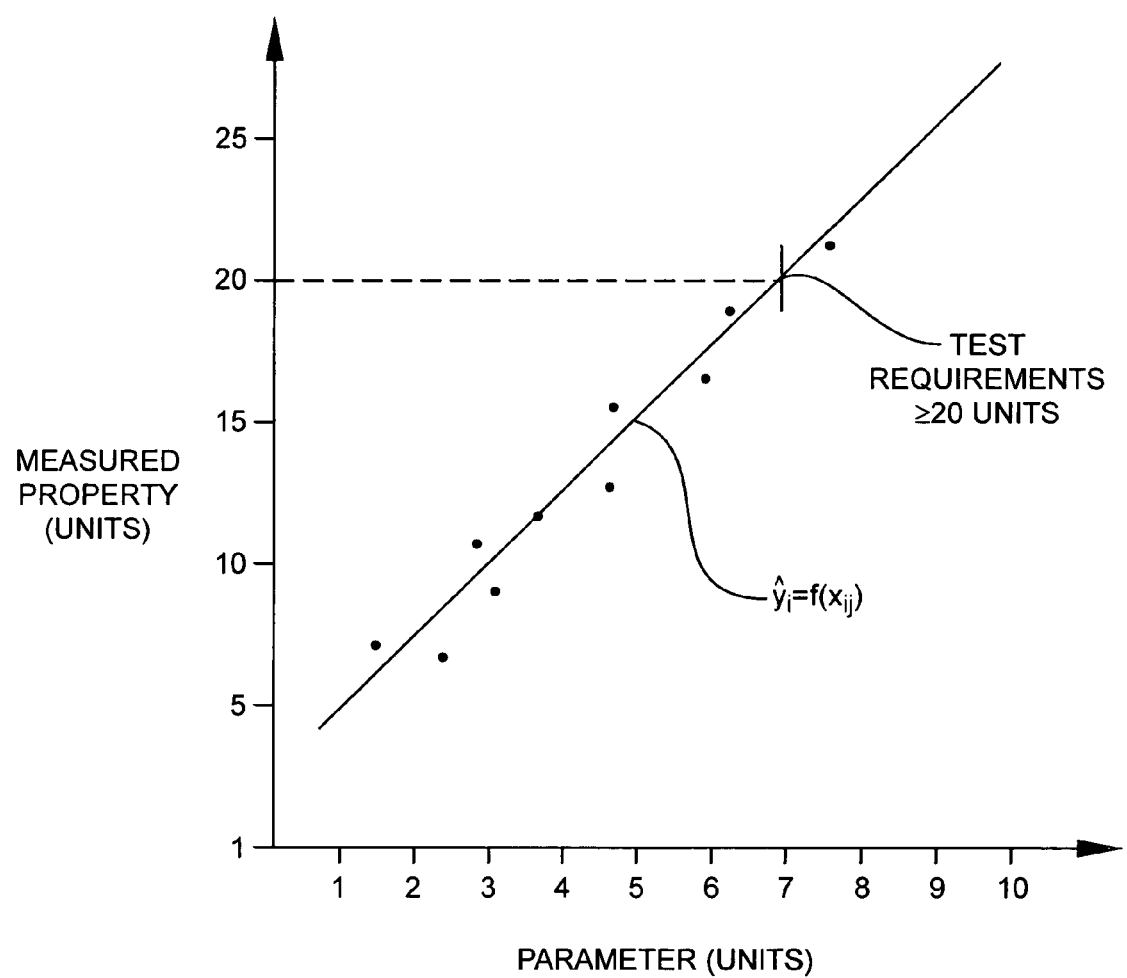
FIG. 2 is a graph of measured indicia of a property of interest determined from a plurality of culture media each containing a respective test peptide from within a peptide library (peptides on x-axis).

Referring to FIG. 2, preferred operations for determining the relationship between the measured indicia of the property of the plurality of first culture media each containing a respective test compound and the parameter(s) of the test compounds can be illustrated by a graphical representation. The calculated values of the d parameter(s) are plotted, and the measured values of the indicia of the property for the n culture media are plotted against the parameter values in d+1 dimensional space. For ease of illustration only, in FIG. 2, n=10 culture media and d=1 parameter.

Conventional line-fitting algorithms can be used to generate a "best fit" line for the plotted data. For example, regression analysis can be utilized to determine a mathematical relationship between the indicia of the property and the value of the parameter for the test compound in each culture medium. The relationship can be represented as $\hat{y}_i = f(x_{ij})$, where $x_{ij}$ denotes a parameter, i ranges from 1 to n where n represents the number of first culture media, j ranges from 1 to d where d represents the number of parameters, and $\hat{y}_i$ represents an estimate of the measured first indicia of the property of the first culture media.

The relationship can be used to identify a second plurality of culture media each containing a respective second test compound which is predicted to provide indicia of the measured property that satisfies the test requirement. In FIG. 2, the test requirement has been established to select for compounds that provide indicia of greater than 20 units. The equation $\hat{y}_i = f(x_{ij})$ can be employed to identify those compounds as components of culture medium that will provide indicia of the property that lie on the upper right portion of the line of FIG. 2 (i.e., provide indicia of the property of greater than 20 units).

Alternatively, a distance function can be calculated to identify compounds, which when added to culture media, are predicted to provide indicia of a property of interest that satisfies a test requirement. In general, the compounds are identified based on their proximity in parameter space to known lead compounds. According to a preferred embodiment, shown in FIG. 3, the present invention is used to identify culture medium components based on the parameters of the culture medium components, Block 300. Operations are performed to measure first indicia of a property of interest for a first plurality of culture media which each contains a first test compound chosen from within a first test library based on a space-filling design, and a test requirement relating to the measured first indicia is determined, Blocks 302 and 304. Operations to carry out Blocks 300, 302 and 304 are as described above for Blocks 100, 102 and 106, respectively.

The distance function can be expressed as $d(x_1, x_2)$ between a first value of a parameter, $x_1$, of a first test compound and a second value of the same parameter, $x_2$, of a second untested compound, Block 306. This relationship will assign to culture media containing a second untested compound an estimated indicia of the property that corresponds to the measured indicia determined from a culture medium containing a first tested compound from the first test library if $d(x_1, x_2) \leq d_{cutoff1}$, where $d_{cutoff1}$ is a cutoff distance for the first test compound, Block 308. In other words, once a lead compound is identified from the first test library, additional lead compounds can be determined based on an assumption that compounds that are close in parameter space will exhibit similar or better activities, Block 310.

In particular embodiments of the invention, $x_1$ and $x_2$ represent a single parameter or, alternatively, a set of parameters, i.e., $x_1 = x_{11}, x_{12}, x_{13}, x_{14} \ldots x_{1k}$ and $x_2 = x_{21}, x_{22}, x_{23}, x_{24} \ldots x_{2k}$, where $k \geq 1$. One specific example of a method of determining a relationship based on distance in parameter space is "nearest neighbor" analysis. Other non-limiting and illustrative methods are cluster analysis, self-organizing maps, and machine learning approaches. See generally, B. B. Ripley Pattern Recognition and Neural Networks, Cambridge University Press, New York (1996). Typically, in this type of analysis, the parameters are established a priori, rather than by determining which parameters to evaluate based on a relationship, as described above.

One particular, and preferred, method of identifying compounds based on a distance function is nearest neighbor analysis. This method can be illustrated using the following simplified example with model data.

According to this illustrative example, the present invention can be used to identify a peptide as a culture medium component, e.g., for mammalian hybridoma cells producing and secreting antibodies. In particular, it is desirable to identify peptides, which when added to culture medium, will promote antibody production by hybridoma cells at a level greater than a test requirement. Four test peptides (Asp-Lys-Ala-His (SEQ. ID NO:23), Asp-Trp-Pro-Ala (SEQ. ID NO:24), Glu-Ser-Met-His (SEQ. ID NO:25), Gly-Val-Asn-Glu (SEQ. ID NO:26); i.e., a training set) may be selected from a peptide library as described above with respect to the QSAR example. Values to describe the various parameters of the peptides, for example, hydrophobicity (i.e., mlogp), molecular weight, and total charge may be calculated for each peptide (Table 5). Each peptide may be added to hybridoma culture medium and antibody production (i.e., biological activity) may be measured for the cells cultured in each culture medium (values shown in Table 5).

TABLE 5

| SEQ ID NO: | Peptide | Hydrophobicity | Mol. Wt | Total Charge | Biol. Act. |
|---|---|---|---|---|---|
| 23 | Asp-Lys-Ala-His | −3.479 | 469.499 | 0 | 15.0 |
| 24 | Asp-Trp-Pro-Ala | −1.608 | 486.505 | −1 | 25.0 |
| 25 | Glu-Ser-Met-His | −3.479 | 501.535 | −1 | 19.3 |
| 26 | Gly-Val-Asn-Glu | −3.421 | 416.411 | −1 | 14.4 |

Assume that there is a second set of untested (i.e., candidate) peptides as shown in Table 6.

TABLE 6

| SEQ ID NO: | Peptide | Hydrophobicity | Mol. Wt | Total Charge | Biol. Act. |
|---|---|---|---|---|---|
| 27 | His-Glu-Asp-Val | −4.03 | 496.477 | −2 | ? |
| 28 | Glu-Thr-Gly-Ser | −4.25 | 391.357 | −1 | ? |
| 29 | His-Try-Gly-Val | −1.278 | 474.518 | 0 | ? |
| 30 | Asp-Phe-Gly-Val | −1.616 | 435.457 | −1 | ? |

The idea of the nearest neighbor rule is to find candidate peptides with parameters that are similar to those from the peptide(s) with the "best" (in this case highest) observed biological activity or the lead peptide(s). Before performing any calculations, typically all parameters will be standardized so that they will each have an equal contribution to the nearest neighbor calculation. In this illustrative example, all parameters may be standardized so that they lie between the values of 0 and 1. This standardization ensures that all parameters will have an equal contribution to the nearest neighbor calculation. A standardized value may be computed in the following manner:

Standardized value=(Original value−Min. value)/
(Max. value−Min. value)          (2)

For example the standardized value of molecular weight for the peptide Asp-Lys-Ala-His (SEQ ID NO:23) may be calculated as follows:

(469.499−391.357)/(501.535−391.357)=0.7092          (3)

The standardized parameter values for the eight peptides are displayed below in Table 7.

TABLE 7

| SEQ ID NO: | Peptide | Hydrophobicity | Molecular Weight | Total Charge |
|---|---|---|---|---|
| 23 | Asp-Lys-Ala-His | 0.2594 | 0.7092 | 1 |
| 24 | Asp-Trp-Pro-Ala | 0.889 | 0.8636 | 0.5 |
| 25 | Glu-Ser-Met-His | 0.2594 | 1 | 0.5 |
| 26 | Gly-Val-Asn-Glu | 0.2789 | 0.2274 | 0.5 |
| 27 | His-Glu-Asp-Val | 0.074 | 0.9541 | 0 |
| 28 | Glu-Thr-Gly-Ser | 0 | 0 | 0.5 |
| 29 | His-Tyr-Gly-Val | 1 | 0.7548 | 1 |
| 30 | Asp-Phe-Gly-Val | 0.8863 | 0.4003 | 0.5 |

Once the standardized values have been calculated, nearest neighbors may be determined by calculating the Euclidean distances between the peptides in this 3-dimensional space (where 3 represents the number of parameters). For example, the distance between Asp-Lys-Ala-His (SEQ ID NO:23) and His-Tyr-Gly-Val (SEQ ID NO:29) is calculated as:

$$SQRT((0.2594-1)^2+(0.7092-0.7548)^2+(1-1)^2)= 0.7420 \quad (4)$$

Table 8 contains these calculated distances between the training set of peptides and the candidate set of peptides.

TABLE 8

|  |  | His-Glu-Asp-Val | Glu-Thr-Gly-Ser | His-Tyr-Gly-Val | Asp-Phe-Gly-Val |
|---|---|---|---|---|---|
| SEQ ID NO:23 | Asp-Lys-Ala-His | 1.0461 | .9057 | .7420 | .8593 |
| SEQ ID NO:24 | Asp-Trp-Pro-Ala | .9604 | 1.2394 | .5236 | .4633 |
| SEQ ID NO:25 | Glu-Ser-Met-His | .5362 | 1.0331 | .9266 | .8675 |
| SEQ ID NO:26 | Gly-Val-Asn-Glu | .9056 | .3599 | 1.0238 | .6315 |

The peptides in the candidate set will then be assigned predicted indicia of the property based the closest peptide in the training set (Table 9). The (hypothetical) biological activities for these four peptides may then be measured as shown in Table 9.

TABLE 9

| Candidate Peptide | Closest Peptide | Predicted Biol. Activity | Observed Activity |
|---|---|---|---|
| His-Glu-Asp-Val (SEQ ID NO:27) | Glu-Ser-Met-His (SEQ ID NO:25) | 19.3 | 18.5 |
| Glu-Thr-Gly-Ser (SEQ ID NO:28) | Gly-Val-Asn-Glu (SEQ ID NO:26) | 14.4 | 10.2 |
| His-Tyr-Gly-Val (SEQ ID NO:29) | Asp-Trp-Pro-Ala (SEQ ID NO:24) | 25.0 | 23.6 |
| Asp-Phe-Gly-Val (SEQ ID NO:30) | Asp-Trp-Pro-Ala (SEQ ID NO:24) | 25.0 | 22.0 |

The test rule is to test candidate peptides that are similar to the best members from the first test library. Thus, in this example, His-Tyr-Gly-Val (SEQ ID NO:29) and Asp-Phe-Gly-Val (SEQ ID NO:30) may be synthesized and tested. If either or both of the peptides satisfy the test requirement, the compound screening process may be stopped at this point. Alternatively, if a compound has not yet been identified, or if additional compounds are desired, the process can be continued in an iterative fashion. As a further alternative, the selection and screening process can be continued using a different relationship, e.g., a QSAR relationship as described above. Finally, as described above, if the first screening yields a suitable compound, it may not be necessary to engage in successive rounds of picking a library and screening additional test compounds.

Figure 4A:
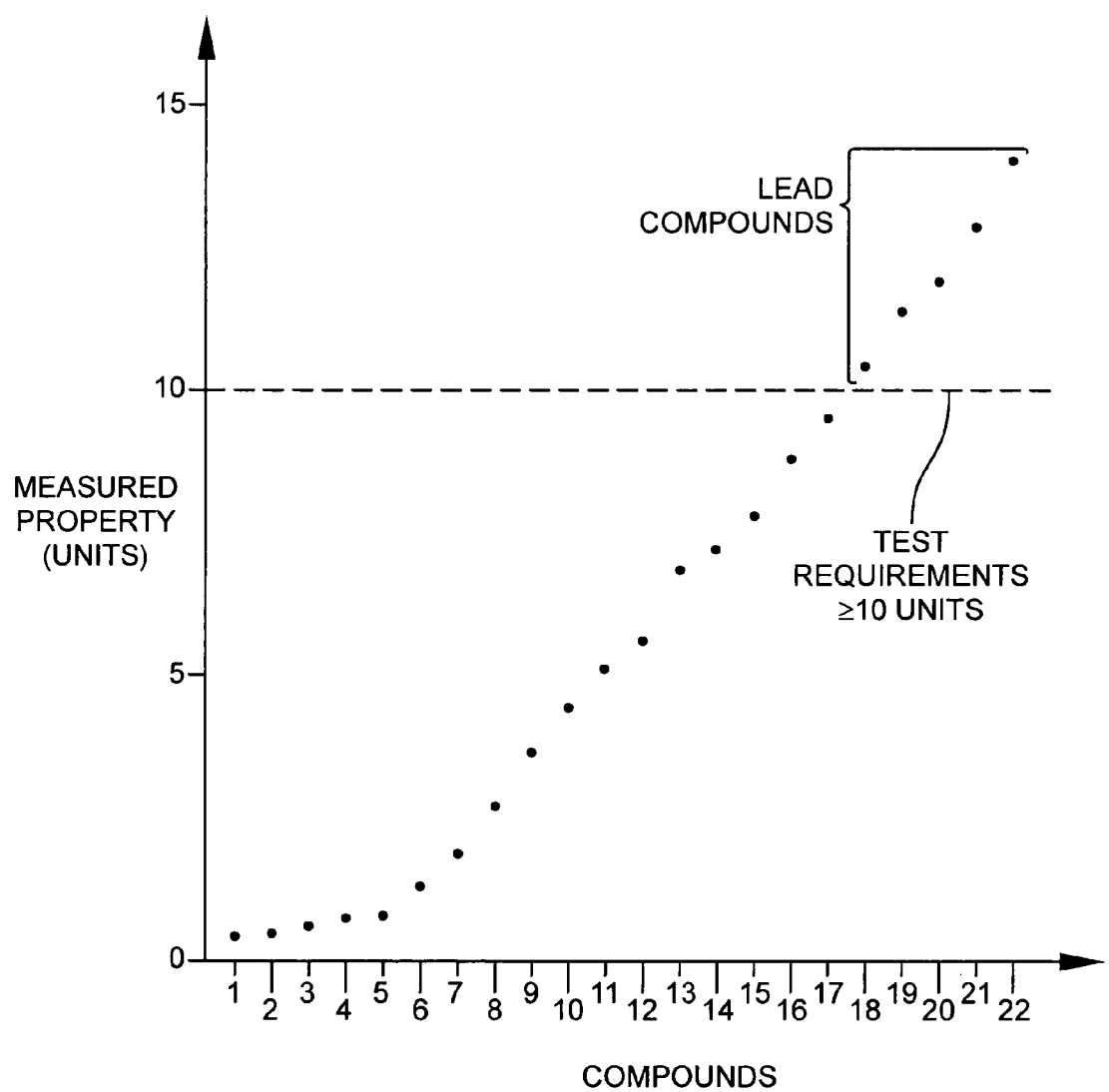
FIG. 4A is a graph of measured indicia of a property of interest determined from a plurality of culture media each containing a respective test peptide from within a peptide library (peptides on x-axis).
Figure 4B:
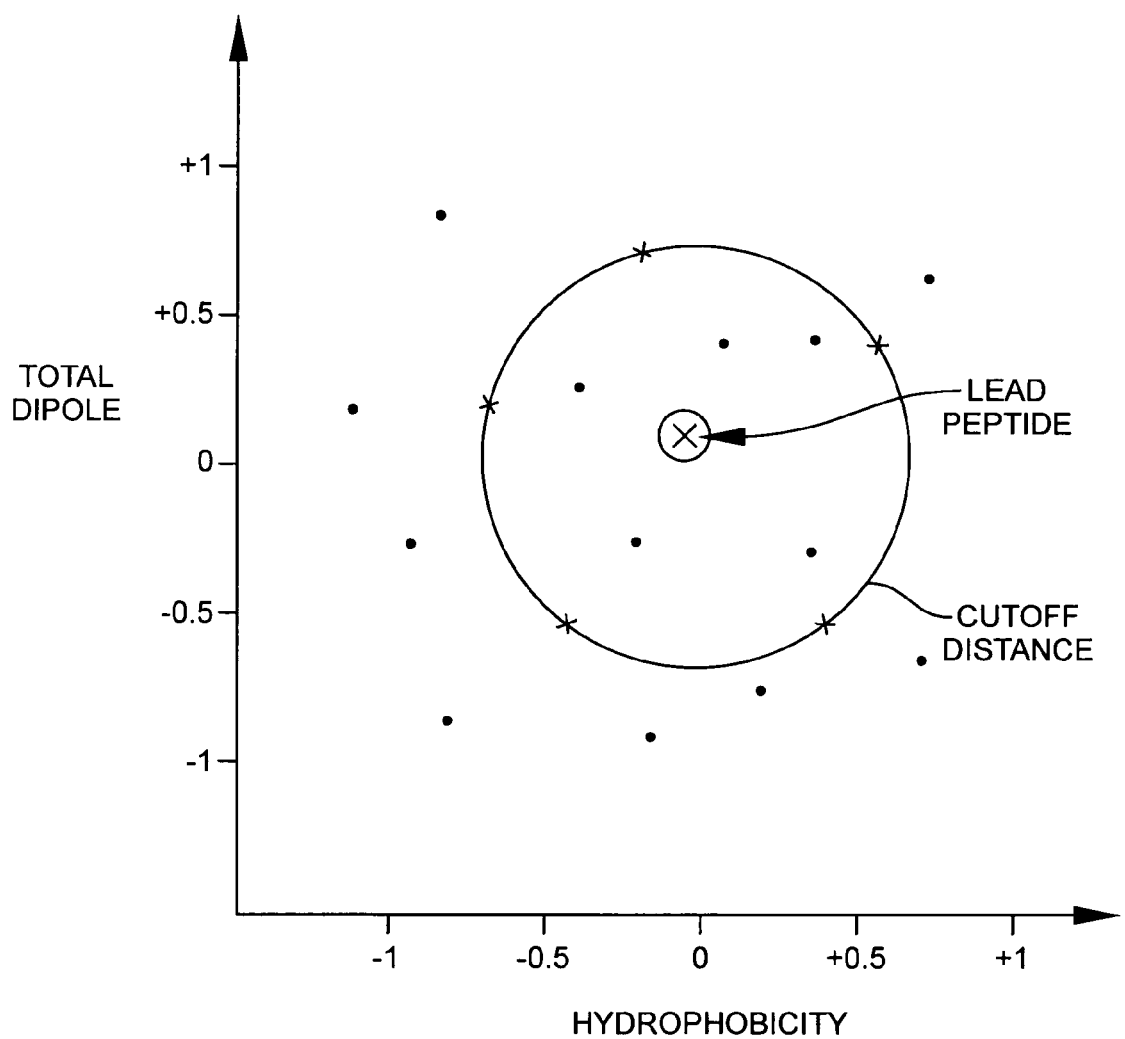
FIG. 4B is a graph of the space surrounding a lead peptide from FIG. 4A with respect to two parameters: total dipole and hydrophobicity. The concentric circles indicate different cut-off points for the distance relationship.

Referring to FIGS. 4A and 4B, the process of identifying a peptide as a component of culture medium using nearest neighbor analysis is graphically represented. After the actual indicia of the property have been measured, the indicia (y-axis) for each peptide (x-axis) may be plotted in ascending (or conversely, in descending) order, FIG. 4A. Those compounds that satisfy the test requirement (in this case, compounds that provide indicia of the property of greater than 10 units when added to culture medium) are selected as lead compounds and the parameter space surrounding some or all of these leads is explored further.

FIG. 4B demonstrates nearest neighbor analysis of a particular lead peptide. For illustrative purposes only, two parameters (e.g., total dipole and hydrophobicity) are employed for the analysis. The standardized values (as described above) for the two parameters are plotted on the x- and y-axis.

Concentric circles can be drawn through the parameter space to represent a particular cut-off in Euclidean distance from the lead peptide. In one particular embodiment, a space-filling design is used to find points in parameter space as indicated by the x's and test the peptides (circles) closest to these points. The reason for extending the space around the lead peptide (i.e., concentric circles) is to gather information as to how close peptides must be in parameter space to exhibit similar activities, characteristics, or indicia of the property (ies) of interest.

The cut-off distance will generally be established for each lead compound. Typically, if the data measured on the first plurality of culture media are clustered together, the cut-off distance will be relatively smaller than if the data points are spread out. Once the cut-off distance has been determined, then a second library of second test compounds that fall within the cut-off space can be identified. The second test compounds are predicted to provide indicia of the property that are similar to or better than the closest lead compound. All or a subset of the second test compounds in the second test library are added to a second plurality of culture media and the actual indicia of the property are measured. For example, a space-filling design can be used to select less than all of the second test library for screening. From this second data set, a final compound for identifying a culture medium component may be identified. Alternatively, a second set of lead compounds can be determined, and nearest neighbor analysis (or some other relationship, e.g., as described by FIG. 1) can be used to identify a third set of compounds for screening. The screening process can continue as many times as necessary to identify compounds exhibiting acceptable or suitable indicia of the property(ies).

It will be appreciated by those skilled in the art that additional operations can be performed to further optimize the above-described methods for identifying a culture medium component. For example, at any stage in the screening process, the number or types of parameters can be changed. In particular, in preferred embodiments, redundant parameters will be identified and eliminated. It is advantageous to identify those parameters that enhance the discrimination among compounds and eliminate redundant parameters to minimize computation complexity and time and to reduce computer storage space. Redundancy of parameters can be determined by any method known in the art, e.g., Principal Component Analysis. Typically, redundant parameters will be highly correlated with an already-existing parameter.

As a further example of process optimization, a cocktail of compounds for use in formulating culture medium can be identified. A cocktail of compounds may give improved results over a single compound alone (e.g., synergy). In addition, once a compound(s) for addition to the culture medium has been identified, the base formulation may be reformulated to further improve the final medium.

Alternatively, reformulation of the base medium may occur at any point in the screening process. Those skilled in the art will appreciate that in some situations it will be advantageous to formulate the base medium so that relatively modest changes in the property of interest can be detected as the effects of lead compounds identified at the early stages of the screening process (which may be relatively small) are masked by some base medium formulations. In other words, a less than optimum base medium may intentionally be selected, at least at the initial stages of the identification process, to maximize the observed impact of the test compounds on cell performance.

A common reason for reformulating media is to move to a defined or at last a semi-defined media, which will typically reduce the variance in performance observed from one lot to the next. The more defined recipes are generally more complex and thereby are labor intensive to prepare. In preferred embodiments of the invention, the addition of the compound(s) identified by the inventive methods will permit the omission or, alternatively, the reduction of one or more medium components. The omitted or reduced component may be an undefined component, e.g., serum or a protein hydrolysate. Alternatively, one or more defined media components may be reduced or omitted, e.g., an amino acid, vitamin, mineral, carbohydrate source, lipid source, and the like. It is also desirable to remove or reduce the presence of certain medium components to minimize production costs and to simplify production processes and quality control. Typically, this process would occur in the final stages of media optimization. Components of the base culture medium would be removed, e.g., one or more components at a time, and the property of interest assayed. An experimental design such as a fractional factorial design may be used to assess the contribution of the particular component(s) to the overall performance of the medium. Those components that have no significant effect on the property of interest can be removed or reduced in the final culture medium formulation. Alternatively, it may be decided that a component does have an effect on the property of interest, but it is omitted or reduced in the formulation because of other considerations, e.g., cost, contaminants, and the like, ie., the advantages are outweighed by the disadvantages of maintaining the component at its current level.

In the screening process, it may further be preferred to screen compounds in both a chemically-undefined culture medium and a more chemically-defined culture medium. This parallel screening need not be carried out concurrently. During the process of reformulating the medium used to culture a particular cell, tissue, organ, etc., it may be preferable to avoid changes to the cellular population in response to the new medium (i.e., subcloning the population). For example, in the process of moving cultured cells from a complex culture medium containing protein hydrolysates to a more defined medium in which peptides are substituted for the protein hydrolysate, changes may be seen in the population of cultured cells. Those skilled in the art will appreciate that it may be desirable that the cultured cells retain the ability to grow in the complex medium (with or without the compound). The parallel screening process described above will assist in maintaining the characteristics of cells cultured therein. In addition, the maintenance of cell viability and growth in undefined and defined media provides an opportunity to identify compounds that enhance performance in both types of media.

The terms "chemically defined" and "chemically undefined" culture media are used herein according to their commonly accepted meanings in the art. In general, a "chemically defined" culture medium is a medium formulation in which essentially all of the components therein are known and are present in known concentrations. Alternatively stated, a "chemically defined" culture medium is one in which essentially all of the components can be described in terms of their chemical formulas and are present in known concentrations. A "chemically undefined" culture medium is one in which the identity and/or concentration of some medium component is unknown and only proportionate values such as total amino nitrogen are obtainable. Thus, any medium containing an undefined component also becomes undefined. The term "semi-defined" is typically used in the art to describe a medium that contains only a small amount of undefined material. Examples of undefined components commonly used in media are yeast extract and fetal calf serum.

In addition, the cells may be "conditioned" or "adapted" prior to the compound screening process by cycling the cells at least once through their current growth medium and the base medium that will be used for the screening process. Typically, the current growth medium is an undefined or semi-defined medium, while the base medium for screening is chemically defined. This conditioning/adaptation process will increase the likelihood that cells will grow in both their former medium as well as in the new base medium. Conditioning/adapting a cell line can enhance the reproducibility of the growth assay and thereby increase assay resolution. In addition, using cells that can grow in both chemically defined and undefined media provides the opportunity to identify medium components for types of media.

As a further optional step, the cells may undergo one or two periods of incubation in base medium alone (i.e., lacking the test compound(s)) prior to being exposed to the test compound(s). Passing the cells through one or more incubation periods in base medium has a two-fold effect. First, it prevents carry-over of undefined components from the previous culture medium, which carry-over may skew the screening results. Second, the incubation period allows the cell to adapt to the new basal medium, so that the measured results should be reflective of the individual test compounds.

It is not necessary that the inventive methods described herein result in a fully-defined culture medium. The final medium formulation may contain serum, protein hydrolysate, or other undefined medium components.

Moreover, the inventive screening methods described herein may be carried out with a base medium from which undefined protein components are absent. Alternatively, the base medium may contain an undefined protein component(s), as long as the effects of lead compounds are not masked by the presence of the undefined protein component. In one particular embodiment in which a medium for culturing bacteria is being formulated, the base medium contains less than about 10% (w/v) (e.g., from about 0.0001% to about 10% (w/v)), preferably about 0.1% (w/v) to about 2.5% (w/v), more preferably about 0.25% (w/v) to about 1% (w/v), of an undefined protein component. In another particular embodiment in which a medium for culturing animal (e.g., mammalian) cells is being formulated, the base medium used in the screening process contains serum. Preferably the serum concentration is from less than about 30% (v/v), more preferably less than about 20% (v/v), in the base culture medium. Alternatively, the serum concentration is preferably from about 0.05% to about 30% (v/v), more preferably 1% (v/v) to about 30% (v/v), still more preferably about 5% (v/v) to about 20% (v/v) in the base culture medium.

Exemplary undefined protein components include but are not limited to hydrolysates (e.g., produced by chemical cleavage such as a casamino acid), digests (e.g., enzymatic digests, such as tryptone, proteose peptone, and the like), extracts (e.g., yeast extract) and infusions (e.g., organ or tissue infusions, such as brain-heart infusions), as those terms are understood in the art. The starting material for the undefined protein component is typically yeast, slaughterhouse offal, milk proteins or other proteins (e.g., gelatin), tissues, or organs. Exemplary sources of sera include but are not limited to fetal calf serum, horse serum, and the like.

Figure 5:
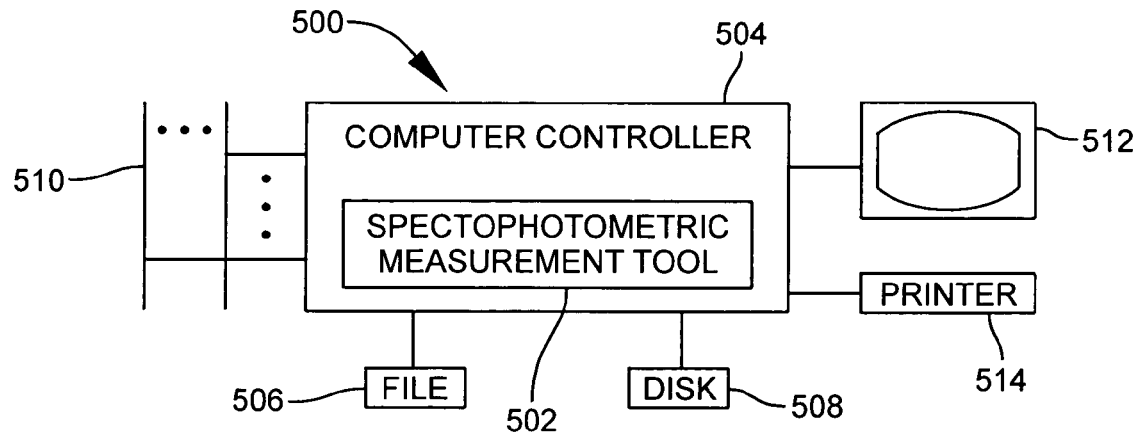
FIG. 5 illustrates a general hardware description of an apparatus for identifying a culture medium component from a compound library according to the present invention.

Another preferred embodiment of the present invention is an apparatus for identifying a compound(s) as a component for culture medium based on at least one parameter(s) of the compound(s). A preferred apparatus 500 is shown in FIG. 5. This preferred apparatus comprises means 502, such as the afore-mentioned measurement tool, for measuring indicia of the property of interest from a plurality of culture media each containing a test compound(s). As described above, any measurement tool known in the art may be used to take measurements as described above, e.g., a spectrophotometer for absorption or colorimetric measurements, a fluorometer or flow cytometer for fluorescence measurements, a scintillation or gamma counter for radioactive measurements, and an automated cell counter, automated plate counter, or manual plate counter for cell number measurements. As a further example, a microwell reader can be used for fluorescence, absorbance or colorimetric measurements. In the preferred apparatus 500, the measurement tool is a spectrophotometer, more preferably, a microwell reader for measuring optical density.

The apparatus 500 also operates under computer control. In particular, the measurement tool 502 is preferably operatively coupled to a general purpose or application specific computer controller 504. The controller 504 preferably comprises a computer program product(s) for controlling operation of the measurement tool 502 and performing numerical operations relating to the above-described steps. The controller 504 may accept set-up and other related data via a file 506, disk input 508, or data bus 510. A display 512 and printer 514 are also preferably provided to visually display the operations performed by the controller 504.

It will be understood by those having skill in the art that the functions performed by the controller 504 may be realized in whole or in part as software modules running on a general purpose computer system. Alternatively, a dedicated stand-alone system with application-specific integrated circuits for performing the above-described functions and operations may be provided. In particular, a preferred computer program product will comprise a computer readable storage medium having computer-readable program code means embodied in the medium. The preferred computer-readable program code means comprises computer-readable program code means for performing the operations described with respect to FIGS. 1 and 3 and throughout the present description.

Figure 6:
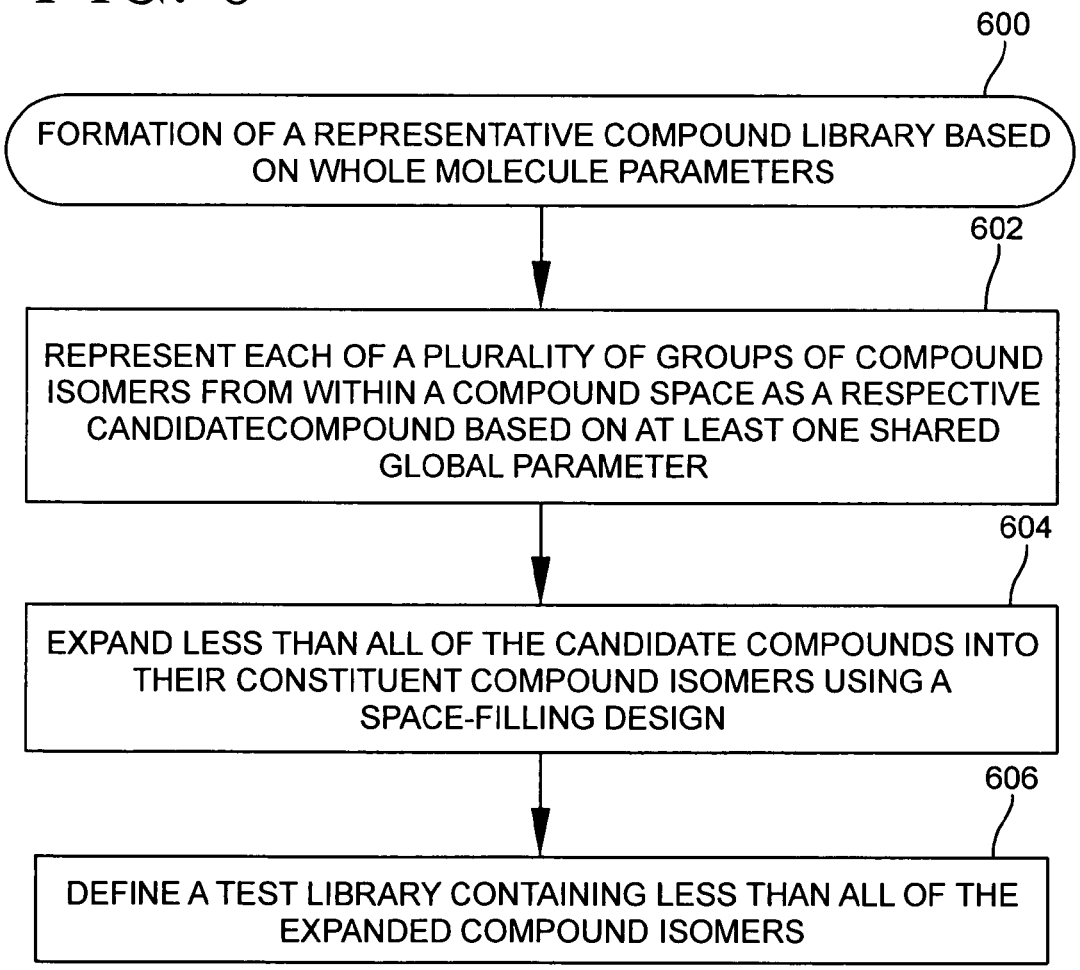
FIG. 6 is a flow chart illustrating operations performed by methods, apparatus and computer program products according to a third embodiment of the present invention.

Turning to FIG. 6, another aspect of the present invention is a method of defining a compound library based on a whole molecule descriptor(s) of the test compounds, Block 600. The compound library is preferably representative of the larger compound space from which it is derived. Thus, this embodiment of the invention provides a method of exploring a relatively large compound space more efficiently and may furthermore obviate computational, time, cost or other restraints: This aspect of the invention can be used with any compound space, in particular, peptide, protein, carbohydrate, nucleic acid, and lipid (e.g., free fatty acids, triglycerols, steroids) compound spaces. Peptide spaces are preferred.

According to the present invention, operations are performed to reduce (i.e., contract) the compound space by classifying all test compounds in the space as a single candidate compound based on a shared global parameter(s) (i.e., a whole molecule parameter), Block 602. The group of compounds sharing common global characteristics are termed "compound isomers". For example, all peptides with the same amino acid composition (i.e., have the same molecular weight) can be grouped as a respective candidate compound. As a further alternative, all peptides having the same chemical formula can be grouped as a single candidate compound (will include peptides with different amino acid sequences, e.g., SVVVV and GIILS, $C_{23}H_{43}N_5O_7$).

In the case of a peptide space, the present investigations have found that a number of parameters may be determined that are independent of peptide sequence. These include, but are not limited to, total charge, molecular weight, logP (i.e., hydrophobicity), and total dipole. In such instances, the order of the amino acids in the sequence is irrelevant, and multiple peptide sequences may be represented by a common sequence. For example, the three peptides AKA, AAK, and KAA contain the same amino acids in the same relative proportions. Consequently, all have the same molecular weight, total charge, etc., even though their sequences are different. Therefore, all three peptides may be represented by a single sequence, such as AAK.

Thus, while AKA, AAK, and KAA are unique structures, their "global" properties may be sufficient for modeling activity. Consequently, all three sequences would yield the same result (e.g., biological activity). Only one peptide may be needed to provide the desired results, and two would be redundant. As a result, fewer peptide sequences would be needed to describe the property space of all peptides of a given length.

In one particular embodiment, as shown in FIG. 6, operations are performed to select less than all of the candidate compounds based on a space-filling design and to re-expand the selected candidate compounds into their constitutive compound isomers, Block 604. Operations to re-expand the compounds function to re-introduce isomer-specific parameters (i.e., sequence-specific parameters). Operations are performed to select the test library from the re-expanded set of compounds using any method known in the art, Block 606. In particular embodiments, at least one (preferably one) compound is selected from each of the expanded groups of compound isomers.

Preferably, the selected test library is representative of the larger compound space, and, likewise, it is preferred that the results achieved by evaluation of the test library are representative of those that would be obtained if the entire compound space was evaluated. Compound libraries generated according to this method can be used for any purpose known in the art, e.g., drug design, media formulation, and the like.

The foregoing aspect of the invention can be illustrated using the following simplified example with model data. The present invention may be used to evaluate a peptide space containing all possible peptide tetramers containing the amino acids A and/or C. There are sixteen possible tetramers if only these two amino acids are utilized (Table 10, column 1). The peptide space containing these sixteen compounds may be contracted by grouping those peptides sharing the same chemical formula (i.e., termed "compound isomers") as five candidate compounds (Table 10, column 2). All peptides with this same whole molecule characteristic (e.g., chemical formula) are treated as a single peptide (i.e., candidate compound) with the same properties. Using any method known in the art (e.g., a space-filling design), two of the five candidate compounds may be selected (Table 10, column 3). The two selected candidate compounds may then be re-expanded into the ten individual compound isomers based on their sequence (Table 10, column 4). In the final step, one of the individual compound isomers is selected from each group (for a total of two peptides) to form the peptide library (Table 10, column 5).

TABLE 10

| SEQ ID NO:32 | AAAA → | AAAA | | |
| SEQ ID NO:33 | AAAC → | AAAC → | AAAC → | AACA |
| SEQ ID NO:34 | AACA | | | AACA |
| SEQ ID NO:35 | ACAA | | | ACAA → ACAA |
| SEQ ID NO:36 | CAAA | | | CAAA |
| SEQ ID NO:37 | AACC → | AACC → | AACC → | CCAA |
| SEQ ID NO:38 | ACAC | | | ACAC |
| SEQ ID NO:39 | CAAC | | | CAAC → CAAC |
| SEQ ID NO:40 | ACCA | | | ACCA |
| SEQ ID NO:41 | CACA | | | CACA |
| SEQ ID NO:42 | CCAA | | | CCAA |
| SEQ ID NO:43 | ACCC → | ACCC | | |
| SEQ ID NO:44 | CACC | | | |
| SEQ ID NO:45 | CCAC | | | |
| SEQ ID NO:46 | CCCA | | | |
| SEQ ID NO:47 | CCCC → | CCCC | | |

In this simplified example, the number of peptides has been reduced from sixteen to two. However, in a more realistic and complex set of circumstances the reduction in the compound space will be significantly greater. Table 11 demonstrates the number of unique peptide sequences possible with increasing peptide length. There is an exponential increase in the number of different peptide sequences possible from the twenty naturally-occurring amino acids with an increase in the size of the peptide. Given X amino acids and a total of Y residues in a peptide sequence, the total number of possible sequences can be calculated as $X^Y$. The total number of peptide sequences for dipeptides through heptapeptides using 20 amino acids are listed in Table 11.

TABLE 11

| Number of Residues | Total Number of Peptides |
|---|---|
| 2 | 400 |
| 3 | 8000 |
| 4 | 160,000 |
| 5 | 3,200,000 |
| 6 | 64,000,000 |
| 7 | 1,280,000,000 |

For example, 8000 different peptide trimers (i.e., sequences of three amino acids) are possible containing the twenty amino acids. This number increases to 64,000,000 for hexapeptides and 1,280,000,000 for heptapeptides. Accordingly, it can be seen that with increasing complexity in compound size and composition, the total compound space can become too vast for efficient exploration thereof.

Given limitations in computational power and disk space, the total number of possible pentamer and longer peptides may be impractical for calculation of sequence-dependent physical parameters. This is significant when the property of interest is dependent on the sequence of the amino acids in the peptide. In such a case, the peptide may be viewed as a series of ordered building blocks. This is the common approach in peptide drug design, where the peptide fits into a highly defined receptor.

Table 12 demonstrates the reduction in the compound space achieved by grouping peptides having a common chemical formula into compound isomers. Although this table was derived empirically, later examination revealed it to be Pascal's triangle (Kotz and Johnson, Eds-in-Chief (1985) *Encyclopedia of Statistical Sciences*, Vol. 6, pp. 628-630, John Wiley & Sons, New York). As one example, the number of peptide heptamers possible from different combinations of the twenty amino acids is reduced to 657,800 by grouping peptides into isomers, as compared with 1,280,000,000 (see Table 11) without grouping of peptide isomers.

TABLE 12

| Residues | 1 | 2 | 3 | 4 | 5 | 6 | 7 |
|---|---|---|---|---|---|---|---|
| 1 | 1 | 1 | 1 | 1 | 1 | 1 | 1 |
| 2 | 2 | 3 | 4 | 5 | 6 | 7 | 8 |
| 3 | 3 | 6 | 10 | 15 | 21 | 28 | 36 |
| 4 | 4 | 10 | 20 | 35 | 56 | 84 | 120 |
| 5 | 5 | 15 | 35 | 70 | 126 | 210 | 330 |
| 6 | 6 | 21 | 56 | 126 | 252 | 462 | 792 |
| 7 | 7 | 28 | 84 | 210 | 462 | 924 | 1716 |
| 8 | 8 | 36 | 120 | 330 | 792 | 1716 | 3432 |
| 9 | 9 | 45 | 165 | 495 | 1287 | 3003 | 6435 |
| 10 | 10 | 55 | 220 | 715 | 2002 | 5005 | 11440 |
| 11 | 11 | 66 | 286 | 1001 | 3003 | 8008 | 19448 |
| 12 | 12 | 78 | 364 | 1365 | 4368 | 12376 | 31824 |
| 13 | 13 | 91 | 455 | 1820 | 6188 | 18564 | 50388 |
| 14 | 14 | 105 | 560 | 2380 | 8568 | 27132 | 77520 |
| 15 | 15 | 120 | 680 | 3060 | 11628 | 38760 | 116280 |
| 16 | 16 | 136 | 816 | 3876 | 15504 | 54264 | 170544 |
| 17 | 17 | 153 | 969 | 4845 | 20349 | 74613 | 245157 |
| 18 | 18 | 171 | 1140 | 5985 | 26334 | 100947 | 346104 |
| 19 | 19 | 190 | 1330 | 7315 | 33649 | 134596 | 480700 |
| 20 | 20 | 210 | 1540 | 8855 | 42504 | 177100 | 657800 |

Figure 7:
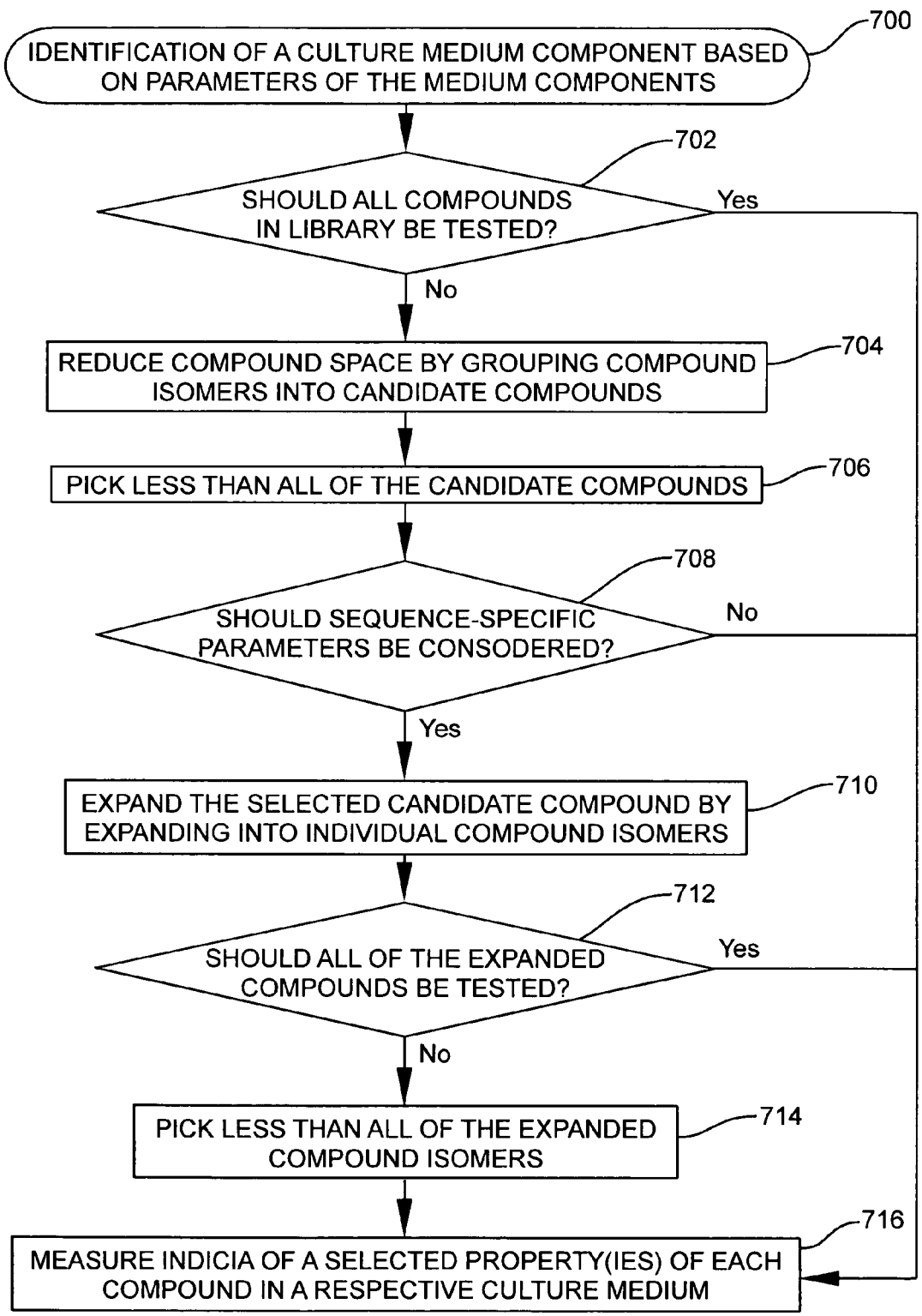
FIG. 7 is a flow chart illustrating operations performed by methods, apparatus and computer program products according to a fourth embodiment of the present invention.

Turning to FIG. 7, the foregoing method of selecting a compound library can be used to identify a compound as a culture media component based on the parameters of the compound as described above, Block 700. A decision is made as to whether all compounds in the compound space need to be screened, Block 702. If it is determined that less than all of the compounds will be tested, operations are performed to reduce the compound space by representing each group of compound isomers within the compound space as a respective candidate compound, Block 704, and to then select less than all of the candidate compounds, Block 706. The decision to test less than all of the compounds in the compound space may be based on any criterion or set of criteria, e.g., cost considerations, time considerations, computational limitations, the nature of the particular property of the compounds being evaluated, etc.

The selected candidate compounds can be screened directly if sequence-specific parameters of the compounds are not deemed important to the selection process. Thus, a decision must be made as to whether sequence-specific parameters should be considered in the screening strategy, Block 708. If sequence-specific parameters are to be considered, then the compounds are expanded into the constituent compound isomers by re-introduction of sequence-specific parameters, Block 710. At this point, all of the expanded compound isomers can be screened, or, alternatively less than all of the expanded compound isomers are selected, Blocks 712 and 714. Again, the decision to test all or less than all of the expanded compound isomers can be made on any basis. Finally, at whatever point in the decision process described above it is decided that a suitable set of compounds for screening has been identified, indicia of a selected property(s) is measured for a plurality of culture media, each containing a respective test compound, Block 716. Operations to identify a compound for use as a culture medium component can be carried out as described above, e.g., in FIG. 1 and FIG. 3.

Turning to FIG. 8, as another preferred embodiment, the invention provides a method of predicting the activity (e.g., biological activity) of a peptide based on at least one whole molecule parameter of the peptide (as defined above), Block 800. Those skilled in the art will appreciate sequence-specific parameters may also be considered in addition to the at least one whole molecule parameter. As used herein, a "biological activity" includes pharmacological and biochemical activities. This method can be used to identify and/or design peptides with particular activities for use as therapeutic drugs (e.g., for medical or veterinary uses), in developing culture media components (as described in more detail above), for identifying and/or designing peptides that interact with a target molecule (e.g., receptor agonists or antagonists) or cell, and in identifying and/or designing peptides that induce or enhance, alternatively, prevent or inhibit, any activity of a target protein (e.g., a receptor, enzyme, signaling protein, cell-surface protein, nucleoprotein, ribosomal protein, and the like), cell, or nucleic acid (e.g., DNA, rRNA, mRNA, tRNA).

Accordingly, it will be apparent to one of skill in the art that this embodiment of the invention can be performed with cultured cells, tissues or organs. Alternatively, this embodiment can also be carried out in cell-free systems (e.g., lysed cells, cell fractions, or biochemically-defined systems such as purified enzymes or receptors).

According to this embodiment of the invention, indicia of a biological activity of interest of a plurality of test peptides from a first test library are measured, Block 802. Peptide libraries are as described hereinabove. The peptides are chosen from the first test library based on a space-filling design, as described in more detail hereinabove. Moreover, the first test peptide may be identified by first reducing a larger peptide space by grouping all of the peptides therein according to at least one whole molecule parameter, e.g., as described above and in FIG. 6.

Indicia of the biological activity may be measured using any suitable method known in the art, as discussed hereinabove with respect to Block 102.

A relationship (e.g., a mathematical relationship) is determined between the measured indicia of the biological activity and at least one whole molecule parameter (e.g., descriptor) of the plurality of first test peptides, Block 804. Operations to determine the relationship are carried out by any means known in the art, preferably, as described above in Blocks 104 and 306. In determining the relationship, sequence-specific parameters (i.e., not whole molecule parameters) may also be considered. Any whole molecule or sequence-specific parameter known in the art for describing peptides may be used to determine the relationship. Whole molecule parameters include, but are not limited to, total charge, molecular weight, isoelectric point, total dipole moment, isotropic surface area, electronic charge, and hydrophobicity. In particular embodiments, at least two whole molecule parameters are employed to describe each of the test peptides. In an alternate preferred embodiment, the peptides are described using at least two whole molecule parameters, where the first parameter is molecular weight and the second is total charge, isoelectric point, total dipole moment, isotropic surface area, electronic charge index, or hydrophobicity.

Referring again to FIG. 8, a test requirement related to the measured indicia of the biological activity is determined, Block 806. Operations to determine the test requirement are performed essentially as described for Blocks 106 and 304. The biological activity of a second peptide or plurality of peptides not within the first set of test compounds can be identified based on the relationship between the biological activity and the whole molecule parameter(s) of the second peptide(s), so as to identify a peptide(s) that is expected to provide indicia of the biological activity that satisfies the test requirement.

In the drawings and specification, there have been disclosed typical preferred embodiments of the invention and, although specific terms are employed, they are used in a generic and descriptive sense only and not for purposes of limitation, the scope of the invention being set forth in the following claims. Moreover, the terminology in the present description relating to graphs, plotting lines, determining a relationship, determining a "best fit" line, representing compound isomers as a candidate compound, expanding candidate compounds into their constituent compound isomers, etc. is intended to include the processing of data and parameters internal to a processing unit (e.g., a computer) containing memory and not limited to the physical acts of printing or plotting lines, curves and graphs.

What is claimed is:

1. A method of identifying a peptide with a desired activity having an indicia that satisfies a test requirement, the method comprising the steps of:

identifying a predetermined set of peptides;

parameterizing the predetermined set of peptides by:

determining a first parameter for each predetermined peptide, wherein the first parameter is a whole molecule parameter, and determining a second parameter for each predetermined peptide, wherein the second parameter is dependent on the specific order of constitutive subunits within each predetermined peptide;

performing a space-filling design of the parameterized peptides to identify first test peptides;

constructing a first test peptide library comprising a plurality of first test peptides identified using the space-filling design, wherein the length of said first test peptides comprises about four amino acids to about twenty amino acids, and wherein said first test peptides are a subset of said predetermined set of peptides;

determining an activity, having an indicia, of said plurality of first test peptides;

measuring the indicia of said activity for said plurality of first test peptides;

deriving a quantitative relationship between said indicia of said activity, said first parameter, and said second parameter;

calculating an estimated indicia for each remaining peptide from said predetermined set of peptides using said quantitative relationship;

setting a test requirement, based on a desired activity, having a test indicia range;

selecting a second test peptide library comprising at least one second test peptide, wherein each second test peptide has an estimated indicia that satisfies said test requirement, and wherein said second test peptides are not in said first test peptide library;

measuring the indicia of each second test peptide; and identifying at least one second test peptide having a measured indicia that satisfies said test requirement.

2. The method of claim 1, wherein said step of deriving a quantitative relationship comprises the step of determining $\hat{y}_i = f(x_{ij})$, where $x_{ij}$ denotes a whole molecule parameter, i ranges from 1 to n where n represents the number of first test peptides in the plurality thereof, j ranges from 1 to d where d represents the number of whole molecule parameters, and $\hat{y}_i$ represents an estimate of the measured indicia of the activity of the plurality of first test peptides.

3. The method of claim 1, wherein said space-filling design expands less than all of the first test peptides into their constituent compound isomers.

4. The method of claim 1, wherein said first parameter is selected from the group consisting of total charge, molecular weight, isoelectric point and total dipole moment.

5. The method of claim 1, wherein said first parameter is selected from the group consisting of total charge, molecular weight, isoelectric point and total dipole moment, and further wherein said second parameter is selected from the group consisting of isotropic surface area, electronic charge index and hydrophobicity.

6. The method of claim 1, wherein said second parameter is selected from the group consisting of isotropic surface area, electronic charge index and hydrophobicity.

7. The method of claim 1, wherein said first parameter is molecular weight and at least one additional parameter is selected from the group consisting of total charge, isoelectric point, total dipole moment, isotropic surface area, electronic charge index, and hydrophobicity.

8. The method of claim 1, wherein the activity is binding to a receptor.

9. The method of claim 1, wherein the activity is enhancement or inducement of a biological activity in a cell.

10. The method of claim 1, wherein the activity is inhibition or prevention of a biological activity in a cell.

11. The method of claim 9 or claim 10, wherein the cell is a cell cultured in vitro.

12. The method of claim 1, wherein the activity is inhibition or prevention of activation of a receptor.

13. The method of claim 1, wherein the activity is enhancement or inducement of activation of a receptor.

14. The method of claim 1, wherein the first test peptide library consists of peptides having a length of no less than four amino acids.

15. The method of claim 1, wherein the first test peptide library consists of peptides having a length of about four to about ten amino acids.

16. A method of identifying a peptide with a desired activity having an indicia that satisfies a test requirement, the method comprising the steps of:

identifying a predetermined set of peptides;

parameterizing the predetermined set of peptides by:

determining a first parameter for each predetermined peptide, wherein the first parameter is a whole molecule parameter, and determining a second parameter for each predetermined peptide, wherein the second parameter is dependent on the specific order of constitutive subunits within each predetermined peptide;

performing a space-filling design of the parameterized peptides to identify first test peptides;

constructing a first test peptide library comprising a plurality of first test peptides identified using the space-filling design, wherein the length of said first test peptides comprises about four amino acids to about twenty amino acids, and wherein said first test peptides are a subset of said predetermined set of peptides;

determining an activity, having an indicia, of said plurality of first test peptides;

measuring the indicia of said activity for said plurality of first test peptides;

deriving a quantitative relationship between said indicia of said activity, said first parameter, and said second parameter;

setting a test requirement, based on a desired activity, having a test indicia range;

selecting a subgroup of first test peptides having an indicia that satisfies said test requirement; and expanding first test peptides from said subgroup into their constituent compound isomers;

performing a space-filling design on said constituent compound isomers to identify candidate peptides;

calculating an estimated indicia for each candidate peptide using said quantitative relationship;

selecting a second test peptide library comprising at least one second test peptide, wherein each second test peptide is a candidate peptide having an estimated indicia that satisfies said test requirement, and wherein said second test peptides are not in said first test peptide library;

measuring the indicia of each second test peptide; and identifying at least one second test peptide having a measured indicia that satisfies said test requirement.

17. A method of identifying a peptide with a desired activity having an indicia that satisfies a test requirement, the method comprising the steps of:

identifying a plurality of initial peptides having a length of about four amino acids to about twenty amino acids;

parameterizing the initial peptides by:

determining a first parameter for each initial peptide, wherein the first parameter is a whole molecule parameter, and determining a second parameter for each initial peptide, wherein the second parameter is dependent on the specific order of constitutive subunits within each initial peptide;

performing a space-filling design of the parameterized peptides to identify first test peptides;

constructing a first test peptide library comprising a plurality of test peptides identified using the space-filling design, wherein said first test peptides are a subset of said initial peptides;

measuring the indicia of an activity of said plurality of test peptides;

deriving a quantitative relationship between said indicia of said activity, said first parameter, and said second parameter of said plurality of test peptides;

calculating an estimated indicia for each initial peptide using said quantitative relationship;

setting a test requirement, based on a desired activity, said test requirement having a test indicia range;

selecting a second test peptide library comprising at least one second test peptide, wherein each second test peptide has an estimated indicia that satisfies said test requirement, and wherein said second test peptides are not in said first test peptide library;

measuring the indicia of each second test peptide; and identifying at least one second test peptide having a measured indicia that satisfies said test requirement.

18. The method of claim 17, wherein said step of performing a space-filling design is performed using a space-filling design that applies a distance function.

19. The method of claim 17, wherein the number of initial peptides in said second test peptide library exceeds a predetermined threshold suited for performing said measuring step, and prior to conducting the step of measuring, performing the steps:

selecting a plurality of new peptides from said first test peptide library to form a new test peptide library using a space filling design;

deriving a new quantitative relationship between said measured indicia, said first parameter, and said second parameter;

calculating an estimated indicia for each initial peptide using said new determined relationship;

selecting a new second test peptide library comprising at least one initial peptide having an estimated indicia that satisfies said test requirement; and repeating said steps of selecting a plurality of new peptides, determining a new relationship, calculating an estimated indicia, and selecting a new second test peptide library until the number of initial peptides in said new second test peptide library does not exceed the predetermined threshold.

20. The method of claim 17, wherein the number of initial peptides in said second test peptide library exceeds a predetermined threshold suited for performing said measuring step, and prior to conducting the step of measuring, performing the steps:

selecting a plurality of new peptides from said first test peptide library to form a new test peptide library using a space filling design;

deriving a new quantitative relationship between said measured indicia, said first parameter, and said second parameter;

calculating an estimated indicia for each initial peptide using said new determined relationship;

selecting a new second test peptide library comprising at least one initial peptide having an estimated indicia that satisfies said test requirement; and repeating said steps of selecting a plurality of new peptides, determining a new relationship, calculating an estimated indicia, and selecting a new second test peptide library until the measured indicia of at least one of the initial peptides in the second test peptide library satisfies a predetermined threshold.

21. A method of identifying a peptide with a desired activity having an indicia that satisfies a test requirement, the method comprising the steps of:

identifying a predetermined set of peptides;

parameterizing the predetermined set of peptides by:
- determining a first parameter for each predetermined peptide, wherein the first parameter is a whole molecule parameter, and
- determining a second parameter for each predetermined peptide, wherein the second parameter is dependent on the specific order of constitutive subunits within each predetermined peptide;

performing a space-filling design of the parameterized peptides to identify first test peptides;

constructing a first test peptide library comprising a plurality of first test peptides identified using the space-filling design, wherein said first test peptides are a subset of said predetermined set of peptides;

determining an activity, having an indicia, of said plurality of first test peptides;

measuring the indicia of said activity for said plurality of first test peptides;

deriving a quantitative relationship between said indicia of said activity, said first parameter, and said second parameter;

calculating an estimated indicia for each remaining peptide from said predetermined set of peptides using said quantitative relationship;

setting a test requirement, based on a desired activity, having a test indicia range;

selecting a second test peptide library comprising at least one second test peptide, wherein each second test peptide has an estimated indicia that satisfies said test requirement, and wherein said second test peptides are not in said first test peptide library;

measuring the indicia of each second test peptide; and identifying at least one second test peptide having a measured indicia that satisfies said test requirement.

* * * * *